US008008011B2

(12) United States Patent
Schmutz et al.

(10) Patent No.: US 8,008,011 B2
(45) Date of Patent: Aug. 30, 2011

(54) GENETIC VARIATION IN PRO-MELANIN-CONCENTRATING HORMONE GENE AFFECTS CARCASS TRAITS IN CATTLE

(75) Inventors: Sheila M. Schmutz, Saskatoon (CA); Sarah C. Helgeson, Saskatoon (CA)

(73) Assignee: University of Saskatchewan, Saskatoon (CA)

(*) Notice: Subject to any disclaimer, the term of this patent is extended or adjusted under 35 U.S.C. 154(b) by 386 days.

(21) Appl. No.: 12/184,018

(22) Filed: Jul. 31, 2008

(65) Prior Publication Data

US 2009/0055211 A1 Feb. 26, 2009

Related U.S. Application Data

(60) Provisional application No. 60/935,190, filed on Jul. 31, 2007.

(51) Int. Cl.
*C12Q 1/68* (2006.01)
(52) U.S. Cl. ............................ 435/6; 435/91.2
(58) Field of Classification Search ........................ None
See application file for complete search history.

(56) References Cited

U.S. PATENT DOCUMENTS 4,683,202 A * 7/1987 Mullis ........................ 435/91.2

OTHER PUBLICATIONS

Wall et al (2003) Nature Reviews. vol. 4, pp. 587-597.*
Mummidi et al (2000) Journal of Biological Chemistry, vol. 275, No. 25, pp. 18946-18961.*
Juppner (1995) Bone vol. 17, No. 2, Supplement, Aug. 1995:39S-42S.*
Hacker et al (1997) Gut 1997; 40:623-627.*
Lucentini (2004) The Scientist. Dec. 20, 2004, p. 20.*
Hegele. Arterioscler Thromb Vasc Biol. 2002; 22:1058-1061.*
Helgeson and Schmutz (GenBank Record having Accession DQ499531.1; GI: 98978958, Apr. 30, 2007).*
Baker, B.I. (1994) Melanin-concentrating hormone updated: Functional considerations, Trends in Endocrinology and Metabolism 5, 120-126.
Barth, A.D., Cates, W.F., & Harland, R.J. (1995) The effect of amount of body fat and loss of fat on breeding soundness classification of beef bulls. Canadian Veterinary Journal 36, 758-764.
Buchanan, F.C., Fitzsimmons, C.J., Van Kessel, A.G., Thue, T.D., Winkelman-Sim, D.C., & Schmutz, S.M. (2002) Association of a missense mutation in the bovine leptin gene with carcass fat content and leptin mRNA levels. Genetics Selection Evolution 34, 105-116.
Casas, E., Stone, R.T., Keele, J.W., Shackelford, S.D., Kappes, S.M., & Koohmaraie, M. (2000) Quantitative trait loci affecting growth and carcass composition of cattle segregating alternative forms of myostatin. Journal of Animal Science 78, 560-569.
Cowell, E.G., Skinner, A., & Hurst, H.C. (1992) Transcriptional Repression by a novel member of the bZIP family of transcription factors. Molecular and Cellular Biology 12, 3070-3077.

Cowell, I.G. (2002) E4BP4/NFIL3, a PAR-related bZIP factor with many roles. BioEssays 24, 1023-1029.
Gavrila, A., Chan, J.L., Miller, L.C., Heist, K., Yiannakouris, N., & Mantzoros, C.S. (2005) Circulating melanin-concentrating hormone, agouti-related protein, and α-melanin-stimulating hormone levels in relation to body composition: Alterations in response to food deprivation and recombinant human leptin administration. The Journal of Clinical Endocrinology and Metabolism 90, 1047-1054.
Ge W., Davis, M.E., Hines H.C., Irvin K.M. & Simmen R.C.M. (2001) Association of a genetic marker with blood serum insulin-like growth factor-I concentration and growth traits in Angus cattle. Journal of Animal Science 79, 1757-62.
Gregory, K.E., Cundiff, L.V., Koch, R.M., Dikeman, M.E., & Koohmaraie, M. (1994) Breed effects and retained heterosis for growth, carcass, and meat traits in advanced generations of composite populations of beef cattle. Journal of Animal Science 72, 833-850.
Helgeson, S.C. (2008) Genetic Variation in Pro-Melanin Concentrating Hormone Affects Carcass Traits in Bos Taurus Cattle. MSC Thesis, University of Saskatchewan.
Ito, M., Gomori, A., Ishihara, A., Oda, Z., Mashiko, S., Matsushita, H., Yumoto, M., Ito, M., Sano, H., Tokita, S., Moriya, M., Iwaasa, H., & Kanatani, A., (2003) Characterization of MCH-mediated obesity in mice. American Journal of Physiology, Endocrinology, and Metabolism 284, E940-E945.
Kapfhamer, D. & Burmeister, M. (1994) Genetic map of the region around grizzled (gr) and mocha (mh) on mouse chromosome 10, homologous to human 19p13.3. Genomics 23, 635-642.
Kappes S.M., Keele J.W., Stone R.T., McGraw R.A., Sonstegard T.S., Smith T.P.L., Lopez-Corrales N. L. & Beattie C.W. (1997) A second-generation linkage map of the bovine genome. Genome Research 7, 235-49.
Lai C.K. & Ting L.P. (1999) Transcriptional repression of human hepatitis B virus genes by a bZIP family member, E4BP4. Journal of Virology 73, 3197-209.
Li, C., Basarab, J., Snelling, W.M., Benkel, B., Kneeland, J., Murdoch, B., Hansen, C., & Moore, S.S. (2004) Identification and fine mapping of quantitative trait loci for backfat on bovine chromosomes 2, 5, 6, 19, 21, and 23 in a commercial line of Bos taurus. Journal of Animal Science 82, 967-972.
Ludwig, D.S., Tritos, N.A., Mastaitis, J.W., Kulkarni, R., Kokkotou, E., Elmquist, J., Lowell, B., Flier, J.S., & Maratos-Flier E. (2001) Melanin-concentrating hormone overexpression in transgenic mice leads to obesity and insulin resistance. The Journal of Clinical Investigation 107, 379-386.
Matys V., Fricke E., Geffers R. et al. (2003) TRANSFAC: transcriptional regulation, from patterns to profiles. Nucleic Acids Research 31, 374-378.
Mitsui, S., Yamaguchi, S., Matsuo, T., Ishida, Y., & Okamura, H. (2001) Antagonistic role of E4BP4 and PAR proteins in the circadian oscillatory mechanism. Genes and Development 15, 995-1006.

(Continued)

*Primary Examiner* — Juliet Switzer

(74) *Attorney, Agent, or Firm* — Heenan Blaikie LLP

(57) ABSTRACT

An A-to-T single nucleotide polymorphism (SNP) identified at position −134 relative to the ATG start codon, in the Pro-Melanin-Concentrating Hormone (PMCH) gene of *Bos taurus* and *Bos indicus* animals of both British and Continental type, is associated with changes in the average fat and grade fat. The A allele occurred in 67% of cattle examined and was associated with higher average fat and grade fat levels. The cattle industry may make use of these findings to genetically select for, and/or sort, cattle using this SNP.

16 Claims, 6 Drawing Sheets

OTHER PUBLICATIONS

Figure 3:
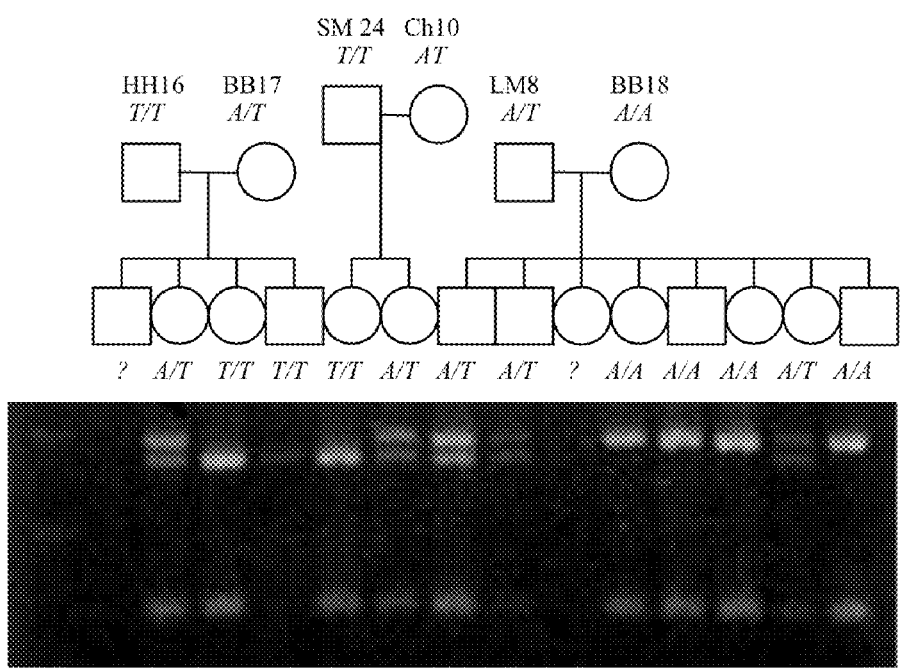

Pedeutour F., Szpirer C. & Nahon J.-L. (1994) Assignment of the human pro-melanin-concentrating hormone gene (PMCH) to chromosome 12q23-q24 and two variant genes (PMCHL1 and PMCHL2) to Chromosome 5p14 and 5q12-q13. Genomics 19, 31-7.

Pissios, P., Bradley, R.L., & Maratos-Flier, E. (2006) Expanding the scales: The multiple roles of MCH in regulating energy balance and other biological functions. Endocrine Reviews 27, 606-620.

Pugh K. (2008) An evaluation of the corticotrophin-releasing hormone and leptin gene SNPs relative to cattle behaviour. MSc Thesis, University of Saskatchewan.

Schenkel, F.S., Miller, S.P., Ye, X., Moore, S.S., Nkrumah, J.D., Li, C., Yu, J., Mandell, I.B., Wilton, J.W., & Williams, J.L. (2005) Association of single nucleotide polymorphisms in the leptin gene with carcass and meat quality traits of beef cattle. Journal of Animal Science 83, 2009-2020.

Schmutz, S.M., Marquess, F.L., Berryere, T.G., & Moker, J.S. (1995) DNA marker-assisted selection of the polled condition in charolais cattle. Mammalian Genome 6, 710-713.

Schmutz, S.M., Buchanan, F.C., Winkelman-Sim, D.C., Pawlyshyn, V., Plante, Y., McKinnon, J.J., & Fournier, B.P. (2001) Development of the Canadian beef reference herd for gene mapping studies. Theriogenology 55, 963-972.

Shimada, M., Tritos, N.A., Lowell, B., Flier, J.S., & Maratos-Flier, E. (1998) Mice lacking melanin-concentrating hormone are hypophagic and lean Nature 396, 670-674.

Skinner, J.D. (1981) Nutrition and fertility in pedigree bulls. In: Environmental factors in mammal reproduction (ed. by D. Gilmore & B. Cook), pp. 160-168. Macmillan, London.

Stone, R.T., Grosse, W.M., Casas, E., Smith, T.P.L., Kelle, J.W., and Bennett, G.L. (2002) Use of bovine EST data and human genomic sequences to map 100 gene-specific bovine markers. Mammalian Genome 13, 211-215.

Viale, A., Zhixing, Y., Breton, C., Pedeutour, F., Coquerel, A., Jordan, D., & Nahon, J-L. (1997) The melanin-concentrating hormone gene in human: Flanking region analysis, fine chromosome mapping, and tissue-specific expression. Molecular Brain Research 46, 243-255.

* cited by examiner

```
   1 gttggtttct atctgatgag tcatttctaa aatgatgwaa gtttttcaag tgctttctat
  61 tcaagctgga aaatatataa aggcaagaat catttacaaa gcaggatgac tgagaaattt
 121 cacttcattt tatacatcct tgtttgactc tatgcaaaca tcaaactaag gatggcaaaa
 181 atgagtttct cttcctacat attaatacta acttttctt tgctttctca aggcatttca
 241 ctttcagcat ccaagtcgat aagaaattta gatgatgaca tggtatttaa aacgttgagg
 301 ctggggaaag cctttcagaa ggaagatacc gcagaaaaat caattgttgt tccttccctg
 361 gagcaatata aaaatgatga gagcagtttc atgaatgatg aagaaaacaa aaattcaaag
 421 gtaagtgata atgcgacttg tcctttattt caatggaaat ttgaatgatc tttatgaatc
 481 ctttgaaagt aaagttgata cttttataag cagaagcacg tgaaaaaaag ttacagtatg
 541 cattagaaca attaaacaaa tttcatacat accaggttgt tcttccattc tgggaaatat
 601 ctcttattca aaaagttttt attccctgaa atcttgtat ctaaagtatt tcttaaaggg
 661 taaaaacagt gcaggcata tttaaattga tcaataagaa tattacacaa ttgtattata
 721 gttccattcc aaatagaaca gttaaaacac aaatcaacct tttctttaca gaatgcaggt
 781 tccaaacata atttcttaaa tcatggcctg ccactgaatc tggctataaa accttatctt
 841 gcactaaaag gatctgtagc ttttccagct gagaatgaag ttcaaaatac tgaatcaaca
 901 caagaaaaaa gagaaattgg ggatgaagaa aactcagcta aatttcctat aggaaggaga
 961 gattttgaca gtgagtagtt tttttaaaat tgaattctta taccttaata tcataaaata
1021 gaactttgaa tttaatggaa tttgggtcca atcataacaa aatcaaacaa gaccatgatt
1081 caacttgtac ttgatactaa gtgactcttg caaaagatgt gaaattaaaa agtatttaat
1141 tagttattac aattgtaatt tactcagatt tagctatact agatccattc tttatttct
1201 aatcaacttt gtgtgatact agtcttctaa acaatttgt ttttccttca gtgcttaggt
1261 gtatgctggg aagagtctat cgaccttgtt ggcaagtctg atgcctgttg gtccacatca
1321 tcatttaaaa agaaagcaaa atcatttaat tgcctctcgg gaaaaaagcc cttaatgttg
1381 ctatgacttg tattatttta aatgtctgtt ttaaaagaaa gtggtattgt tatgcctaaa
1441 tgattgcttt acttgtgcat taaactttat gaattttatg cataattatg act
```

Exon 1 (nt. 172 to 420)
MAKMSFSSYILILTFSLLSQGISLSASKSIRNLDDDMVFKTLRLGKAFQKEDTAEKSIVVPSLEQYKNDESSFMN
DEENKNSK Exon 2 (nt. 772-970)
NAGSKHNFLNHGLPLNLAIKPYLALKGSVAFPAENEVQNTESTQEKREIGDEENSAKFPIGRRDFD Exon 3 (nt. 1252-1301)
MLRCMLGRVYRPCWQV Protein sequence (exons 1, 2 and 3)
MAKMSFSSYILILTFSLLSQGISLSASKSIRNLDDDMVFKTLRLGKAFQKEDTAEKSIVVPSLEQYKNDESSFMN
DEENKNSKNAGSKHNFLNHGLPLNLAIKPYLALKGSVAFPAENEVQNTESTQEKREIGDEENSAKFPIGRRDFDM
LRCMLGRVYRPCWQV

Figure 1

```
-171   gttggtttct atctgatgag tcatttctaa aatgatgWaa gtttttcaag
-121   tgctttctat tcaagctgga aaatatataa aggcaagaat catttacaaa
-71    gcaggatgac tgagaaattt cacttcattt tatacatcct tgtttgactc
                                                  tcct tgtttgactc
-21    tatgcaaaca tcaaactaag gATGGCAAAA ATGAGTTTCT CTTCCTACAT
       tatgcaaaca tcaaactaag gATGGCAAAA ATGAGTTTCT CTTCCTACAT
+30    ATTAATACTA ACTTTTTCTT TGCTTTCTCA AGGCATTTCA CTTTCAGCAT
       ATTAATACTA ACTTTTTCTT TGCTTTCTCA AGGCATTTCA CTTTCAGCAT
+80    CCAAGTCGAT AAGAAATTTA GATGATGACA TGGTATTTAA AACGTTGAGG
       CCAAGTCGAT AAGAAATTTA GATGATGACA TGGTATTTAA AACGTTGAGG
+130   CTGGGGAAAG CCTTTCAGAA GGAAGATACC GCAGAAAAAT CAATTGTTGT
       CTGGGGAAAG CCTTTCAGAA GGAAGATACC GCAGAAAAAT CAATTGTTGT
+180   TCCTTCCCTG GAGCAATATA AAAATGATGA GAGCAGTTTC ATGAATGATG
       TCCTTCCCTG GAGCAATATA AAAATGATGA GAGCAGTTTC ATGAATGATG
+230   AAGAAAACAA AAATTCAAAG gtaagtgata atgcgacttg tcctttattt
       AAGAAAACAA AAATTCAAAG
+280   caatggaaat ttgaatgatc tttatgaatc ctttgaaagt aaagttgata
+330   cttttataag cagaagcaag tgaaaaaaag ttacagtatg cattagaaca
+380   attaaacaaa tttcatacat accaggttgt tcttccattc tgggaaatat
+430   ctcttattca aaaagttttt attccctgaa aatcttgtat ctaaagtatt
+480   tcttaaaggg taaaaacagt gcaggcata tttaaattga tcaataagaa
+530   tattacacaa ttgtattata gttccattcc aaatagaaca gttaaaacac
+580   aaatcaacct tttctttaca gAATGCAGGT TCCAAACATA ATTTCTTAAA
                              AATGCAGGT TCCAAACATA ATTTCTTAAA
+630   TCATGGCCTG CCACTGAATC TGGCTATAAA ACCTTATCTT GCACTAAAAG
       TCATGGCCTG CCACTGAATC TGGCTATAAA ACCTTATCTT GCACTAAAAG
+680   GATCTGTAGC TTTTCCAGCT GAGAATGAAG TTCAAAATAC TGAATCAACA
       GATCTGTAGC TTTTCCAGCT GAGAATGAAG TTCAAAATAC TGAATCAACA
+730   CAAGAAAAAA GAGAAATTGG GGATGAAGAA AACTCAGCTA AATTTCCTAT
       CAAGAAAAAA GAGAAATTGG GGATGAAGAA AACTCAGCTA AATTTCCTAT
+780   AGGAAGGAGA GATTTTGACA gtgagtagtt ttttaaaat tgaattatta
       AGGAAGGAGA GATTTTGACA
+830   taccttaata tcataaaata gaactttgaa tttaatggaa tttgggtcca
+880   atcataacaa aatcaaacaa gaccatgatt caacttgtac ttgacactaa
+930   gtgactcttg caaaagatgt gaaattaaaa agtatttaat tagttattac
+980   aattgtaatt tactcagatt tagctatact agatccattc ttttatttct
+1030  aatcaacttt gtgtgatact agtcttctaa acaattttgt ttttccttca
+1080  gTGCTTAGGT GTATGCTGGG AAGAGTCTAT CGACCTTGTT GGCAAGTCTG
        TGCTTAGGT GTATGCTGGG AAGAGTCTAT CGACCTTGTT GGCAAGTCTG
+1130  Atgcctgttg gtccacatca tcatttaaaa agaaagcaaa atcatttaat
       At
+1180  tgcctctcgg gaaaaaagcc cttaatgttg ctatgacttg tattatttta
+1230  aatgtctgtt ttaaaagaaa gtggtattgt tatgcctaaa tgattgcttt
+1280  acttgtgcat taaactttat gaattttatg cataattatg act
```

Figure 2

```
B. taurus:      MAKMSFSSYI  LILTFSLLSQ  GISLSASKSI  RNLDDDMVFK
H. sapiens:     **NL  ***F  L***  *******N
M. musculus:    **TL*M  *M*A*F  L***  *EIN
R. norvegic:    ***L*M  *M*A***F*H  L***  VEIN B. taurus:      TLRLGKAFQK  EDTAEKSIVV  PSLEQYKNDE  SSFMNDEENK
H. sapiens:     *F**G*  *****VIA  ******  E***
M. musculus:    *F*M******  *****R*V*A  **********  *G****DD**
R. norvegic:    *F*M******  *****R*V*A  ****G*****  *G**K*DDD*
                                                       NGE
B. taurus:      NSKNAFSKHN  FLNHGLPLNL  AIKPYLALKG  SVAFPAENEV
H. sapiens:     ****TG****  **********  **********  *******G*
M. musculus:    ****TG**Q*  LVT*****S*  *V********  *******G*
R. norvegic:    TTTGQ*  LVT*****S*  *V******  PAV**G*
                             NEI                       MCH
B. taurus:      QNTESTQEKR  EIGDEENSAK  FPIGRRDFDM  LRCMLGRVYR
H. sapiens:     **********  **********  **********  **********
M. musculus:    A***  ******  ******  ********
R. norvegic:    **********  **********  **********  **********

B. taurus:      PCWQV.
H. sapiens:     ******
M. musculus:    ******
R. norvegic:    ******
```

Figure 4

```
Cattle  --------GTTGGTTTCTATCTGATGAGTCATTTCTAAAATCATGAAA-GT
Human   CATAAACGTTAGCCTGAATCTAATGAGTCATTTCTAAAATCATCAAAAGT
Rat     TACAAACGCGAGGCTTACGGGGTGATTCATTTCTAAAAAG---AAAAG- Cattle  -------TTTTCAAGTGCTTTCTATTCAAGCTGGAAAATATATAAAGGCAA
Human   ATAATTCTTTCAAGTGCTTTCTATTCAAGCTAGCAAATATATAAAGATAC
Rat     ATAAGGCCTTCAAGTGTTTTCTATTCAGGC-ACAAGTATATAAAGGTA- Cattle  G-AATCATTTACAAAGCAG
Human   AGAATCCTTTACCAAGCAG
Rat     GGAATCATTCAGTCGCCAG
```

Figure 6

GENETIC VARIATION IN PRO-MELANIN-CONCENTRATING HORMONE GENE AFFECTS CARCASS TRAITS IN CATTLE

RELATED APPLICATIONS

This application claims the benefit of the filing date of provisional application No. 60/935,190 filed on Jul. 31, 2007.

FIELD

The invention relates to an allelic polymorphism of the Pro-Melanin-Concentrating Hormone (PMCH) gene, methods of management of livestock animals based on this polymorphism and the use of the polymorphism for selective breeding.

BACKGROUND

In managing livestock animals using present methods, visible characteristics or phenotypic traits are used to predict how an animal will grow, and thus how the animal should be fed to most profitably achieve market condition. The object of a livestock industry is to convert feed into meat, and much is known about growth patterns of livestock.

Fat deposition, or the amount of intramuscular fat and back fat on an animal carcass, is important to industry participants because carcasses exhibiting desired amounts and proportions of such fats can often be sold for higher prices than carcasses that exhibit divergences from such desired amounts and proportions. Further, the desired carcass fat deposition often varies among different markets and buyers, and also often varies with time in single markets and among particular buyers in response to public demand trends with respect to desired of fat and marbling in meat.

Weight gain by a livestock animal during its growth and development typically follows a tri-phasic pattern that is carefully managed by commercial producers and finishers. The efficiency of dietary caloric (feed) conversion to weight gain during an increment of time varies during three growth phases; a first phase of growth comprises that portion of a livestock animal's life from birth to weaning, and is not paid much heed by commercial feeding and finishing operators.

A second growth phase comprises that portion of a livestock animal's life from weaning to attainment of musculoskeletal maturity. Feed conversation efficiency is relatively high during this phase; livestock producers usually restrict caloric intake, which has the effect of causing this phase to be prolonged but also typically results in animals with larger frames, which is the aim of dietary management during this phase. During the second growth phase weight gain is associated with skeletal mass and muscle mass accumulation primarily.

During a third growth phase, after an animal has attained musculoskeletal maturity, the efficiency of feed conversion is reduced, such that it requires more feed to increase an animal's weight. Thus, during the second phase of growth, a typical steer could convert 5 to 6 pounds of feed into one pound of weight gain. Upon entering the third phase, feed conversion efficiency typically decreases, such that 7 up to 10 or more pounds of feed are required to produce one pound of gain.

During the third phase livestock feeders significantly increase the caloric content of animals' rations. During the third growth phase weight gain is associated with fat accumulation primarily. In a steer weighing 900 pounds at the end of the second phase, of that 900 pounds, typically 350 pounds will be red meat. At the end of the third phase, the steer would typically weigh 1400 pounds and typically 430 pounds will be red meat.

In the cattle industry, initially a cow/calf operator will breed bulls to cows, birth calves from the cows, and allow the calves to feed on their mother's milk until they are weaned some months after birth. This is the first phase of growth of the calf.

After weaning, the calf enters the second stage of growth where it is fed to grow to its full skeletal size. This commonly called the "backgrounding" phase during which musculoskeletal maturity is achieved. When the animal has reached its full size, it enters the third phase of growth where the fully grown animal puts on weight.

Typically it is at the start of the third stage of growth that the animal enters a finishing feed lot. In the feed lot the object is to feed the animal the proper ration so that it will most quickly obtain the proper market characteristics that are desired at that given time. At present, for instance it is desirable to have beef that is well marbled, i.e., it has considerable intramuscular fat in the meat. At other times it may be desirable to have lean meat with very little intramuscular fat. The price the feed lot owner attains for cattle when sold to the packer can vary significantly depending on marbling of the meat.

Presently, cattle entering a feed lot are divided into groups according to phenotypic characteristics such as estimated age, frame size, breed, weight and so forth. By doing this the feed lot owner is attempting to group the cattle so that the group can be penned together and fed the same ration and will be ready for market at the same time.

The phenotype of an animal is the visible characteristics of the animal, which results from the interaction between the animal's genetic makeup and its environment. Conventional management techniques group cattle according to uniform phenotypic traits and then keep the environment constant for each animal in the group in hopes that the group will together achieve a different phenotype at some later date. The genetic makeup of any individual steer is a significant factor in the ability of that individual steer to grow in the same manner as another steer of the same phenotype.

Considerable variation in phenotypes is observed at the end of the third phase among cattle that entered the third phase with a substantially uniform phenotype, despite having been subjected to the same environmental factors as with conventional management methods. It is not uncommon for a pen of cattle, each having a weight within a range of 100 pounds going into a feeding pen, to have weights varying in a range of 300 pounds or more coming out of the pen for slaughter. It is also known that the feed conversion rate of cattle varies to some degree. Since feed represents a major cost to the feed-lot operator, it is more profitable to feed those cattle with a higher feed conversion rate, since an animal that converts a ton of feed into 200 pounds of saleable body weight is more profitable than an animal that converts the same ton of feed into only 180 pounds of saleable meat.

The timing of slaughter is based on the mean visible condition of the group of cattle in each pen, resulting in a wide variation in carcass weight and ensuring that grading premiums for carcasses of a desired condition of weight and fat are not met for a significant number of cattle. In a typical pen, a number of the cattle in the pen would have been at the desired carcass condition earlier, but by the time they are slaughtered they are over fat. Similarly, many cattle could readily achieve the desired carcass condition if fed longer. However, conventional management techniques require that all the cattle in the pen are slaughtered at the same time.

A dairy cattle operator is faced with similar issues as packers, feeders and cow/calf operators. Dairy cattle are also segregated into groups based upon phenotypic traits even though genotype can affect milk production. In particular, the time period from calving through to peak lactations is the most stressful period in the life of the dairy cow. During this time, the animal usually falls into negative energy balance because the daily feed intake, although increased, is unable to keep pace with the increased energy demand of lactation. Since certain genotypes affect energy balance, management of animals by genotype will be important for efficient dairy production. Furthermore, the animals' genetic predisposition to lay down fat also impacts milk production.

It is well known to those skilled in the art that single nucleotide polymorphisms (SNPs) can provide a useful way in which to distinguish different alleles of a gene. Furthermore, when the presence of a SNP can be associated with a specific phenotype, the SNP operates as a powerful marker and can be used to predict phenotypic outcomes based on an animal's genotypic makeup. By identifying animals with a particular genotype, with respect to SNP alleles, it is possible to identify or select for animals that display desirable phenotypes, as compared to animals lacking the desired genotype.

In the beef cattle industry in many countries, animals that gain weight better than their counterparts are more desirable because they finish faster. Producers receive the most money when the animal has an optimal layer of fat, and are penalized for overly thin or overly fat animals. As a result of this, genes that influence the appetite pathway are of particular interest to the industry. Identification and characterization of the genes involved in appetite and metabolism aids producers in the selection of the best possible animals that will produce the most monetary gains.

The gene for Pro-Melanin-Concentrating Hormone (PMCH) encodes three neuropeptides: Neuropeptide-Glycine-Glutamic Acid (NGE), Neuropeptide-Glutamic Acid-Isoleucine (NEI), and Melanin-Concentrating Hormone (MCH) (Nahon et al. 1989). MCH is the most extensively studied product of PMCH. MCH has been shown to stimulate feed intake, as well as to modulate metabolic function in rodents (reviewed by Pissios et al. 2006). MCH is predominantly expressed in the mammalian hypothalamus and has also been shown to be expressed in other tissues including the thyroid, spleen, intestine, and testes of mice and rats (Baker 1994). The role of MCH in the appetite pathway has been supported by findings that MCH mRNA is up-regulated in fasted mice (Shimada et al. 1998) and humans (Gavrilla et al. 2005), and that MCH knock-out mice are lean, exhibiting decreased appetite and increased metabolic rate (Shimada et al. 1998). Conversely, over expression of MCH has been shown to lead to obesity and insulin resistance, mediated by increased appetite and reduced metabolism (Ito et al. 2003; Ludwig et al. 2001).

PMCH has been mapped in a number of mammalian species. In humans PMCH is located on chromosome 12q23-q24 (Pedeutour et al. 1994), on mouse chromosome 10 (Kapfhamer & Burmeister 1994), and on cattle chromosome 5 (Stone et al. 2002). Evidence that PMCH may play a role in fat production in cattle comes from the findings that quantitative trait loci (QTL) for backfat exist in the same region of BTA5 (Casas et al. 2000; Li et al. 2004). Thus, the identification of polymorphisms in PMCH that are causal or that are linked to important carcass traits in cattle could allow the implementation of accurate and inexpensive genetic assays to identify or select for animals that display a desirable phenotype.

FIGURES

FIG. 1: Sequence of the Bos taurus PMCH genomic DNA (accession number DQ499531) [SEQ ID NO: 1] and upstream region, and corresponding amino acid sequence of exon 1 [SEQ ID NO: 2], exon 2 [SEQ ID NO: 3], exon 3 [SEQ ID NO: 4] and pre-pro-MCH [SEQ ID NO: 5]. The A-to-T (g.−134 SNP) at position −134 relative to the ATG start codon is at position 38 in this Figure and is represented by a W. The putative TATA box is underlined.

FIG. 2: Alignment of sequenced Bos taurus PMCH genomic DNA (accession number DQ499531) [SEQ ID NO: 1] and brain cDNA (accession number EF175214) [SEQ ID NO: 6] from this study. cDNA sequence is shaded. Lower case letters represent intronic sequence. The A-to-T polymorphism at position −134 nucleotides upstream of the ATG start codon (g.−134 SNP) is represented by a W. The putative TATA box is underlined. Exon 1 is putatively located at nucleotides −69 to +249; exon 2 is located at nucleotides +601 to +799; exon 3 is located at nucleotides +1081 to +1130.

FIG. 3: Gel photograph showing the results of PMCH genotyping by RFLP.

FIG. 4: PMCH amino acid alignment of Bos taurus (accession number EF175214), Homo sapiens (accession number NM_002674), Mus musculus (accession number NM_029971), and Rattus norvegicus (accession number NM_012625.1) pre-pro-MCH. Bos taurus NGE [SEQ ID NO: 7], NEI [SEQ ID NO: 8], and MCH [SEQ ID NO: 9], are shaded.

Figure 5:
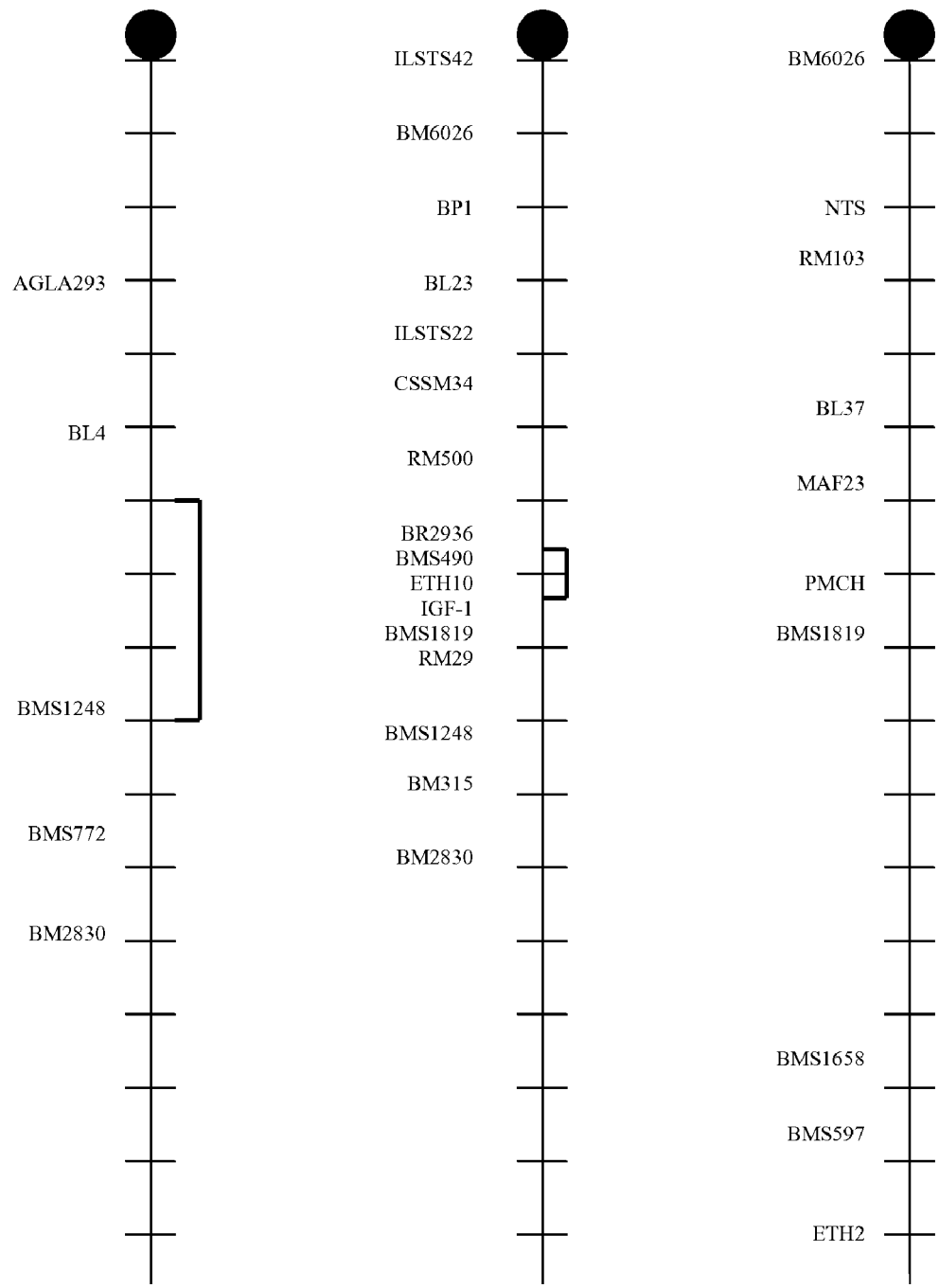

FIG. 5: Linkage mapping of microsatellites and PMCH on BTA5. Each line represents approximately 10 cM. The boxes indicate the regions containing putative quantitative trait loci for backfat level.

FIG. 6: Alignment of the promoter regions from cattle, human, and rat PMCH. Shaded areas represent conservations with cattle sequence. The g.−134 A-to-T SNP is indicated by a W. The putative TATA box is underlined as is the first nucleotide of exon 1. The putative E4BP4 binding site is shown in dark grey. The cattle sequence is from accession number DQ499531; the rat sequence is from NC_005106.2. Adapted from Viale et al. 1997, with the addition of cattle sequence.

SUMMARY

The inventors demonstrate herein that cattle with an adenosine nucleotide at position g.−134 (g.−134A allele) relative to the start translation codon of the PMCH gene lay down grade fat and average fat more readily than those with the thymine nucleotide (g.−134T allele) at this position. The inventors also demonstrate that the g.−134A allele is significantly associated with lower shear force values and better palatability in beef.

The g.−134T allele is present in 30% of the crossbred cattle analysed, which would have a significant effect on performance of feedlot cattle in Canada. Cattle producers are expected to produce cattle with consistent amounts of lean meat and fat. A DNA test to select stock based on the allele at position −134 relative to the start translation codon of the PMCH gene can be used in alone or in conjunction with other tests currently available, to further improve carcass quality and consistency. For example, by selecting g.−134AA cattle, feedlot animals can be sorted in order to finish them faster and produce more tender cuts of meat. Producers can use the invention herein disclosed to genetically sort cattle upon feedlot entry, thus optimizing the quality of the carcasses produced and maximizing the consistency of the finished beef product.

The present invention provides nucleic acid sequences and methods of using them, which permit the prediction and modulation (control) of average fat and grade fat deposition in *Bos* sp. animals, and the shear force values and palatability of beef.

In one aspect the invention is a method of identifying *Bos* sp. animals having a polymorphism associated with higher grade fat depth and higher average fat depth, lower shear force and improved palatability, which method comprises the steps of:
(a) isolating a nucleic acid sample from the animal, and
(b) determining whether the nucleotide at position 38 in SEQ ID NO: 1, in the nucleic acid sample, is an "A" residue, "T" residue or both,
wherein the "A" residue is associated with higher grade fat depth and higher average fat depth, lower shear force and improved palatability than the "T" residue.

In one embodiment of this method, the nucleic acid sample is a DNA sample.

In one embodiment of this method, step (b) is performed by amplifying a region of the nucleic acid sample using an oligonucleotide primer pair, to form nucleic acid amplification products comprising the nucleotide at position 38 in SEQ ID NO: 1. At least one primer of the oligonucleotide pair may comprise at least 10 contiguous nucleotides of the nucleic acid sequence of SEQ ID NO: 1 or a complement thereof.

In one embodiment the polymorphism is identified by performing PCR amplification using a primer having SEQ ID NO: 18 and a primer having SEQ ID NO: 13 and the DNA amplification products are analysed by digestion with restriction endonuclease TaiI.

In another embodiment of the method, step (b) is performed by determining whether a second polymorphism that is linked with the nucleotide at position 38 in SEQ ID NO: 1, is present or absent.

In one embodiment, the second polymorphism is linked with the "T" nucleotide that at position 38 in SEQ ID NO: 1. In another embodiment, the second polymorphism is linked with the "A" nucleotide that at position 38 in SEQ ID NO: 1.

In another aspect the invention is a method of regulating the time to finishing, in a group of *Bos* sp. animals entering a feedlot, said method comprising the steps of:
(a) determining whether the animals in the group have an "AA", "AT" or "TT" genotype at position 38 in SEQ ID NO: 1, and
(b) providing each animal in the group a diet that is selected according its genotype at position 38 in SEQ ID NO: 1.

In one embodiment, at step (b) the diet selected for each animal is also selected according to its phenotype upon entering the feedlot.

In one embodiment of this method, the animals in the group finish at the same selected time with approximately the same grade fat depth and average fat depth. In another embodiment of this method the animals in the group finish at different selected times but with approximately the same grade fat depth and average fat depth.

In yet another aspect, this invention is a method of improving the quality and consistency of the carcasses obtained from a group of *Bos* sp. animals from a feedlot, which method comprises the steps of:
(a) genotyping the animals in the group to determine whether they have an "AA", "AT" or "TT" genotype at position 38 in SEQ ID NO: 1,
(b) sorting the animals into sub-groups according to their genotype at position 38 in SEQ ID NO: 1, and
(c) feeding the animals in any one sub-group the same diet for the same length of time.

In one embodiment, at step (b) the animals are sorted into sub-groups also on the basis of their phenotype on entering the feedlot.

In another aspect the invention is a method of breeding *Bos* sp. animals, based on the knowledge of the animals' genotype, comprising the steps of:
(a) determining the genotype at position 38 in SEQ ID NO: 1 in the animals, wherein the genotype will be one of "AA", "AT", or "TT" at this position, and
(b) selecting a first animal and a second animal for breeding, on the basis of their genotype at this position.

In various embodiments the first animal and second animal are selected so as to produce offspring with a genotype selected from the group consisting of:
(a) an "AA" genotype at position 38 in SEQ ID NO: 1;
(b) an "AT" genotype at position 38 in SEQ ID NO: 1, and
(c) a "TT" genotype at position 38 in SEQ ID NO: 1.

In another aspect the invention is a method of increasing the grade fat depth and average fat depth, lowering the shear force and improving palatability, in a selected group of *Bos* sp. animals, comprising:
(a) determining a genetic predisposition of *Bos* sp. animals to have higher average fat depth and higher grade fat depth, lower shear force and better palatability, by determining their genotype at position 38 in SEQ ID NO: 1, and
(b) selecting animals that have the "A" allele at position 38 in SEQ ID NO: 1 for inclusion in the group.

In another aspect the invention is a method of identifying those *Bos* sp. animals which have an allele associated with lower shear force and better palatability of beef, by determining the genotype of the *Bos* sp. animals at position 38 in SEQ ID NO: 1, wherein animals that have the A-allele have the allele that is associated with lower shear force and better palatability.

The present invention also provides the genomic and cDNA sequences for the Bos taurus PMCH gene, and for *Bos taurus* pre-pro-PMCH, NGE, MEI and MCH, and methods of using them and making them.

Thus, in another aspect the invention is an isolated DNA molecule comprising SEQ ID NO: 1 or a variant or a portion thereof.

In another aspect the invention is an isolated DNA molecule comprising SEQ ID NO: 6 or a variant or a portion thereof.

In another aspect, the invention is an isolated DNA molecule that encodes a polypeptide having the amino acid sequence of SEQ ID NO: 5 or SEQ ID NO: 7.

In another aspect the invention is an isolated DNA molecule that encodes a polypeptide with at least 90% amino acid sequence identity to SEQ ID NO: 5.

In another aspect the invention is an isolated polypeptide comprising the amino acid sequence of SEQ ID NO: 5.

In another aspect the invention is an isolated polypeptide comprising the amino acid sequence of SEQ ID NO:7.

DETAILED DESCRIPTION

The *Bos taurus* PMCH gene, and upstream and downstream regions, have been sequenced in order to identify genetic variants and to evaluate whether these variants affect carcass traits. An A-to-T single nucleotide polymorphism (SNP) has been identified at position −134 relative to the ATG start codon (g.−134A-to-T) of the PMCH gene. This polymorphism is shown at position 38 in SEQ ID NO: 1.

As used herein, g.−134 means the nucleotide that is at position −134 relative to the ATG start codon of the PMCH gene, as demonstrated in FIGS. 1, 2 and 6. In FIG. 2, g.−134 is nucleotide number −134 and the ATG start codon begins at nucleotide number +1. In FIG. 1, g.−134 is nucleotide number 38 and the ATG start codon begins at nucleotide number 172.

As used herein, g.−134A or g.−134T means that the nucleotide at position g.−134 is an A or a T, respectively. Thus, g.−134A or g.−134T means that the A allele or the T allele, respectively, is at this location in SEQ ID NO: 1. An animal that is g.−134AA or g.−134TT is a homozygote for the A allele or the T allele respectively, at this location in SEQ ID NO: 1, and an animal that is g.−134AT is a heterozygote.

The invention is based in part on the inventors' finding that alleles at g.−134 are significantly associated with average fat and grade fat depth in Bos sp. The g.−134A allele is associated with higher average fat and grade fat depth in animals, lower shear force values, and better palatability in beef, as compared to the g.−134T allele.

"Grade fat" as used herein is the fat depth in millimeters at the leanest point of fat cover on the fourth-quarter of the rib eye measured either on the carcass or by ultrasound. (Canadian Beef Grading Agency)

"Average fat" as used herein is the fat depth arrived at by dividing the rib eye into quarters and taking the fat measurement at the three points of the division which quarter the rib eye on the fat edge, and then averaging them, measured either on the carcass or by ultrasound. (Canadian Beef Grading Agency)

"Backfat" as used herein means all the fat on cattle that lies along their back and sides, under the skin, outside the main muscle masses. This term encompasses grade fat and average fat.

Fat "depth" may alternatively be referred to as fat "level" or fat "thickness".

"Shear force" as used herein is a reference to the Warner-Bratzler Shear Force value was developed by Bratzler in 1932 and is a quantitative measurement of the tenderness of cooked meat.

"Palatability" as used herein is the overall sensory experience of the beef, including flavour, juiciness, and tenderness.

The practice of the present invention will employ, unless indicated specifically to the contrary, conventional methods of molecular biology and recombinant DNA techniques within the abilities of those skilled in the art. Many of these techniques are described below for the purpose of illustration. Such techniques are explained fully in the literature. See, e.g., Sambrook, et al. *Molecular Cloning: A Laboratory Manual*, Cold Spring Harbor Laboratory Press, Cold Spring Harbor, N.Y. (2000); Maniatis et al. *Molecular Cloning: A Laboratory Manual* (1982); Ausubel, F. M. et al. (eds.) *Current Protocols in Molecular Biology*, John Wiley and Sons, Inc. (2007); Kirby, *DNA Fingerprinting, An Introduction*, WH Freeman & Co., New York (1992).

Selection and Breeding

The invention is the use of the g.−134 polymorphism for genotyping Bos sp. animals, by determining whether the A or T nucleotides are present at position g.−134, in a sample of nucleic acid from the animals. Genotyping Bos sp. animals using the polymorphism of the present invention can be used to identify and select for animals having the g.−134A allele, who are likely to have the associated phenotype of a higher average fat and grade fat depth, and the resultant lower shear force values and better palatability. Thus, the use of genetic assays to identify the polymorphism disclosed herein, will find use in breeding or selection of Bos sp. animals with desirable traits.

Genetic assay-assisted selections for genotype are important in that they allow decisions to be made with respect to an individual animal. In particular, the cattle industry can use these findings to sort feedlot animals by genotype, in order to better control the time to finishing, the quality of the carcass obtained, and the consistency of the beef product. An animal with a g.−134AA genotype, for example, would be expected to finish faster than an animal with a g.−134TT genotype, when both are fed the same diet. On the other hand, if a lean grade of beef was desired, animals with a g.−134TT genotype may be advantageous over animals with a g.−134AA genotype.

The invention is also a method of regulating the time to finishing, in a group of Bos sp. animals entering a feedlot, by determining which nucleotides are present at position g.−134 in both alleles of the PMCH gene in the animals, and then making decisions as the amount and/or type of feed that the animals will receive, based on their g.−134 genotype and their phenotype when entering the feedlot. For example, it may be desirable to have all animals in a group finish closer in time to one another, and thus animals with a g.−134TT genotype may be fed more (or a different type of feed) than animals with a g.−134AA genotype. Alternatively, it may be desirable to identify animals with a g.−134TT genotype and to separate them from the animals with a g.−134AA or a g.−134AT genotype, knowing that the animals will finish at different times.

The invention is also a method of improving the quality and consistency of average fat depth and grade fat depth in the carcasses obtained from a group of Bos sp. animals from a feedlot, or the quality and consistency of the shear force and palatability in beef produced from these animals, which method involves genotyping the animals to determine whether they have an "AA", "AT" or "TT" genotype at position 38 in SEQ ID NO: 1, sub-grouping the animals according to their genotype at g.−134 and perhaps also their phenotype upon entry to the feedlot, and feeding each sub-group the same diet for the same period of time. For example, it may be desirable to separate (physically or virtually) animals with a g.−134TT genotype and similar phenotypes, from the animals with a g.−134AA or a g.−134A T genotype, and feed them for a longer period of time, so that these animals finish with the same quality and consistency of product as the animals having the g.−134AA or a g.−134AT genotype. Or, it may be desirable to feed cattle that are most genetically predisposed to laying down fat, the g.−134AA genotype, to achieve a high fat grade, and to feed cattle that are least genetically predisposed to laying down fat, the g.−134TT genotype, so as to achieve a lean grade. Animals with the g.−134AT allele are advantageous as they may be fed to achieve either a fat grade or a lean grade.

This invention is also a breeding program directed at optimization of average fat and grade fat depth in a cattle herd. The polymorphism at g.−134 can be used to select cows and bulls, in order to produce a herd of cattle that have the desired g.−134 alleles, thereby generating a herd of cattle that have a selected and consistent average fat and grade fat depth. A desired average fat and grade fat may be obtained by producing a herd of cattle that have a g.−134AA genotype, or it may be obtained by producing a herd of cattle that have a g.−134AT genotype, or it may be obtained by producing a herd of cattle that have a g.−134TT genotype. Preferably, the cattle in the herd will have a g.−134AA genotype, or a g.-134AT genotype, and most preferably the cattle in the herd will have a g.-134AA genotype.

Genetic assay-assisted selections for animal breeding are important in that they allow selections to be made without the need for raising and phenotypic testing of progeny. In particular, such tests allow selections to occur among related individuals that do not necessarily exhibit the trait in question.

Methods of Genotyping Animals
General

In accordance with the invention, any assay which identifies animals based upon g.-134 allelic differences may be used and is specifically included within the scope of this invention.

One of skill in the art will recognize that, having identified a causal polymorphism for a particular associated trait, or a polymorphism that is linked to a causal mutation, there are an essentially infinite number of ways to genotype animals for this polymorphism. The design of such alternative tests merely represents a variation of the techniques provided herein and is thus within the scope of this invention as fully described herein. Illustrative procedures are described herein below.

Non-limiting examples of methods for identifying the presence or absence of a polymorphism include single-strand conformation polymorphism (SSCP) analysis, RFLP analysis, heteroduplex analysis, denaturing gradient gel electrophoresis, temperature gradient electrophoresis, ligase chain reaction and direct sequencing of the gene.

Non-limiting examples of amplification methods for identifying the presence or absence of a polymorphism include polymerase chain reaction (PCR), strand displacement amplification (SDA), nucleic acid sequence based amplification (NASBA), rolling circle amplification, T7 polymerase mediated amplification, T3 polymerase mediated amplification and SP6 polymerase mediated amplification.

Techniques employing PCR™ detection are especially advantageous in that detection is more rapid, less labor intensive and requires smaller sample sizes. Primers are designed to detect a polymorphism at g.-134 (position 38 in SEQ ID NO: 1). Primers that may be used in this regard may, for example, comprise regions of SEQ ID NO: 1 and complements thereof. However, as is apparent, in order to detect a polymorphism at g.-134, neither of the PCR primers in a primer pair need comprise regions of SEQ ID NO: 1 or a complement thereof, and both of the PCR primers in the pair may lie in the genomic regions flanking the genomic location of SEQ ID NO: 1 in cattle. However, preferably at least one primer of the oligonucleotide primer pair comprises at least 10 contiguous nucleotides of the nucleic acid sequence of SEQ ID NO: 1 or a complement thereof.

A PCR™ amplified portion of SEQ ID NO: 1 can be screened for a polymorphism, for example, with direct sequencing of the amplified region, by detection of restriction fragment length polymorphisms produced by contacting the amplified fragment with a restriction endonuclease having a cut site altered by the polymorphism, or by SSCP analysis of the amplified region. These techniques may also be carried out directly on genomic nucleic acids without the need for PCR™ amplification, although in some applications this may require more labor.

Once an assay format has been selected, selections may be unambiguously made based on genotypes assayed at any time after a nucleic acid sample can be collected from an individual animal, such as a calf, or even earlier in the case of testing of embryos in vitro, or testing of fetal offspring.

As used herein, "*Bos* sp." means a *Bos taurus* or a *Bos indicus* animal, or a *Bos taurus/indicus* hybrid animal, and includes an animal at any stage of development, male and female animals, beef and dairy animals, any breed of animal and crossbred animals. Examples of beef breeds are Angus, Beefinaster, Hereford, Charolais, Limousin, Red Angus and Simmental. Examples of dairy breeds are Holstein-Freisan, Brown Swiss, Guernsey, Ayrshire, Jersey and Milking Shorthorn.

Any source of nucleic acid from an animal may be analysed for scoring of genotype. Preferably, the nucleic acid used is genomic DNA. In one embodiment, nuclear DNA that has been isolated from a sample of hair roots, ear punches, blood, saliva, cord blood, amniotic fluid, semen, or any other suitable cell or tissue sample of the animal is analyzed. A sufficient amount of cells are obtained to provide a sufficient amount of DNA for analysis, although only a minimal sample size will be needed where scoring is by amplification of nucleic acids. The DNA can be isolated from the cells or tissue sample by standard nucleic acid isolation techniques.

In another embodiment samples of RNA, such as total cellular RNA or mRNA, may be used. RNA can be isolated from tissues expressing PMCH, by standard nucleic acid isolation techniques, and may be purified or unpurified. The RNA can be reverse transcribed into DNA or cDNA.

Hybridization of Nucleic Acids

The use of a probe or primer of between 13 and 100 nucleotides, preferably between 17 and 100 nucleotides in length, or in some aspects of the invention up to 1-2 kilobases or more in length, allows the formation of a duplex molecule that is both stable and selective. Molecules having complementary sequences over contiguous stretches greater than 20 bases in length are generally preferred, to increase stability and/or selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production. The invention specifically provides probes or primers that correspond to or are a complement of SEQ ID NO: 1 or a portion thereof.

Accordingly, nucleotide sequences may be used in accordance with the invention for their ability to selectively form duplex molecules with complementary stretches of DNAs or to provide primers for amplification of DNA from samples. Depending on the application envisioned, one would desire to employ varying conditions of hybridization to achieve varying degrees of selectivity of the probe or primers for the target sequence.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand.

For certain applications, lower stringency conditions may be preferred. Under these conditions, hybridization may occur even though the sequences of the hybridizing strands are not perfectly complementary, but are mismatched at one or more positions. Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Hybridization conditions can be readily manipulated depending on the desired results.

In certain embodiments, it will be advantageous to employ nucleic acids of defined sequences with the present invention in combination with an appropriate means, such as a label, for determining hybridization. For example, such techniques may be used for scoring of RFLP marker genotype. A wide variety of appropriate indicator means are known in the art, including fluorescent, radioactive, enzymatic or other ligands, such as avidin/biotin, which are capable of being detected. In certain embodiments, one may desire to employ a fluorescent label or an enzyme tag such as urease, alkaline phosphatase or peroxidase, instead of radioactive or other environmentally undesirable reagents. In the case of enzyme tags, calorimetric indicator substrates are known that can be employed to provide a detection means that is visibly or spectrophotometrically detectable, to identify specific hybridization with complementary nucleic acid containing samples.

In general, it is envisioned that probes or primers will be useful as reagents in solution hybridization, as in PCR™, for detection of nucleic acids, as well as in embodiments employing a solid phase. In embodiments involving a solid phase, the sample DNA is adsorbed or otherwise affixed to a selected matrix or surface. This fixed, single-stranded nucleic acid is then subjected to hybridization with selected probes under desired conditions. The conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. After washing of the hybridized molecules to remove non-specifically bound probe molecules, hybridization is detected, and/or quantified, by determining the amount of bound label. Representative solid phase hybridization methods are disclosed in U.S. Pat. Nos. 5,843,663, 5,900,481 and 5,919,626. Other methods of hybridization that maybe used in the practice of the present invention are disclosed in U.S. Pat. Nos. 5,849,481, 5,849,486 and 5,851,772. The relevant portions of these and other references identified in this section of the specification are incorporated herein by reference.

Amplification of Nucleic Acids

Nucleic acids used as a template for amplification may be isolated from cells, tissues or other samples according to standard methodologies. Amplification can occur by any of a number of methods known to those skilled in the art.

The term "primer", as used herein, is meant to encompass any nucleic acid that is capable of priming the synthesis of a nascent nucleic acid in a template-dependent process. Typically, primers are short oligonucleotides from ten to twenty and/or thirty base pairs in length, but longer sequences can be employed. The primers are complementary to different strands of a particular target DNA sequence. This means that they must be sufficiently complementary to hybridize with their respective strands. Therefore, the primer sequence need not reflect the exact sequence of the template. Primers may be provided in double-stranded and/or single-stranded form, although the single-stranded form is preferred. Primers may, for example, comprise regions of SEQ ID NO: 1 and complements thereof.

Pairs of primers designed to selectively hybridize to nucleic acids are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids containing one or more mismatches with the primer sequences. Once hybridized, the template-primer complex is contacted with one or more enzymes that facilitate template-dependent nucleic acid synthesis. Multiple rounds of amplification, also referred to as "cycles", are conducted until a sufficient amount of amplification product is produced.

The amplification product may be detected or quantified. In certain applications, the detection may be performed by visual means. Alternatively, the detection may involve indirect identification of the product via chemiluminescence, radioactive scintigraphy of incorporated radiolabel or fluorescent label or even via a system using electrical and/or thermal impulse signals (Affymax technology).

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, each of which is incorporated herein by reference in their entirety.

Other amplification techniques may comprise methods such as nucleic acid sequence based amplification (NASBA), rolling circle amplification, T7 polymerase mediated amplification, T3 polymerase mediated amplification and SP6 polymerase mediated amplification.

Another method for amplification is ligase chain reaction ("LCR"), disclosed in European Application No. 320,308, incorporated herein by reference in its entirety. U.S. Pat. No. 4,883,750 describes a method similar to LCR for binding probe pairs to a target sequence. A method based on PCR™ and oligonucleotide ligase assay (OLA), disclosed in U.S. Pat. No. 5,912,148, also maybe used.

An isothermal amplification method, in which restriction endonucleases and ligases are used to achieve the amplification of target molecules that contain nucleotide 5'-[alpha-thio]-triphosphates in one strand of a restriction site also may be useful in the amplification of nucleic acids in the present invention (Walker et al, 1992).

Strand Displacement Amplification (SDA), disclosed in U.S. Pat. No. 5,916,779, is another method of carrying out isothermal amplification of nucleic acids which involves multiple rounds of strand displacement and synthesis, i.e., nick translation.

Detection of Amplified Nucleic Acids

Following any amplification, it may be desirable to separate the amplification product from the template and/or the excess primer. In one embodiment, amplification products are separated by agarose, agarose-acrylamide or polyacrylamide gel electrophoresis using standard methods. Separated amplification products may be cut out and eluted from the gel for further manipulation. Using low melting point agarose gels, the separated band may be removed by heating the gel, followed by extraction of the nucleic acid.

Separation of nucleic acids also may be effected by chromatographic techniques known in art. There are many kinds of chromatography which may be used in the practice of the present invention, including adsorption, partition, ion-exchange, hydroxylapatite, molecular sieve, reverse-phase, column, paper, thin-layer, and gas chromatography as well as HPLC.

In certain embodiments, the amplification products are visualized. A typical visualization method involves staining of a gel with ethidium bromide and visualization of bands under UV light. Alternatively, if the amplification products are integrally labeled with radio- or fluorometrically-labeled nucleotides, the separated amplification products can be exposed to x-ray film or visualized under the appropriate excitatory spectra. Another typical method involves digestion of the amplification product(s) with a restriction endonuclease that differentially digests the amplification products of the alleles being detected, resulting in differently sized digestion products of the amplification product(s).

In one embodiment, following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, or another binding partner carrying a detectable moiety.

In particular embodiments, detection is by Southern blotting and hybridization with a labeled probe. The techniques involved in Southern blotting are well known to those of skill in the art (see Sambrook et al, 1989). One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Linkage with Another Marker

A genetic map represents the relative order of genetic markers, and their relative distances from one another, along each chromosome of an organism. During meiosis in higher organisms, the two copies of each chromosome pair align themselves closely with one another. Genetic markers that lie close to one another on the chromosome are seldom recombined, and thus are usually found together in the same progeny individuals ("linked"). Markers that lie close together show a small percent recombination, and are said to be "linked". Markers linked to loci that are associated with phenotypic effects (e.g., SNP's associated with phenotypic effects) are particularly important in that they may be used for selection of individuals having the desired trait. The identity of alleles at these loci can, therefore, be determined by using nearby genetic markers that are co-transmitted with the alleles, from parent to progeny. As such, by identifying a marker that is linked to such an allele, this will allow direct selection for the allele, due to genetic linkage between the marker and the allele.

Those of skill in the art will therefore understand that when genetic assays for determining the identity of the nucleotide at position g.−134 are mentioned herein, this specifically encompasses detection of genetically linked markers (e.g., polymorphisms) that are informative for the g.−134 locus. Such markers have predictive power relative to the traits of grade fat and average fat depth, because they are linked to the g.−134 locus. Such markers may be detected using the same methods as described herein for detecting the polymorphism at the g.−134 locus. It is understood that these linked markers may be variants in genomic sequence of any number of nucleic acids, however SNP's are particularly preferred.

In order to determine if a marker is genetically linked to the g.−134 locus, a lod score can be applied. A lod score, which is also sometimes referred to as $Z_{max}$, indicates the probability (the logarithm of the ratio of the likelihood) that a genetic marker locus and a specific gene locus are linked at a particular distance. Lod scores may e.g. be calculated by applying a computer program such as the MLINK program of the LINKAGE package (Lathrop et al., 1985; Am J. Hum Genet 37(3): 482-98). A lod score of greater than 3.0 is considered to be significant evidence for linkage between a marker and the g.−134 locus. Thus, if a marker (e.g., polymorphism) and the g.−134 locus have a lod score of greater than 3, they are "linked", according to the present invention.

Other Assays

Other methods for genetic screening may be used within the scope of the present invention, include denaturing gradient gel electrophoresis ("DGGE"), restriction fragment length polymorphism analysis ("RFLP"), chemical or enzymatic cleavage methods, direct sequencing of target regions amplified by PCR™ (see above), single-strand conformation polymorphism analysis ("SSCP") and other methods well known in the art.

Kits

All the essential materials and/or reagents required for screening cattle for the g.−134 allele in accordance with this invention may be assembled together in a kit. This generally will comprise a probe or primers designed to hybridize to the nucleic acids in the nucleic acid sample collected. Also included may be enzymes suitable for amplifying nucleic acids (e.g., polymerases such as reverse transcriptase or Taq polymerase), deoxynucleotides and buffers to provide the necessary reaction mixture for amplification. Such kits also may include enzymes and/or other reagents suitable for detection of specific nucleic acids or amplification products.

PMCH Nucleic Acids and Proteins

In one aspect, the invention is an isolated DNA molecule comprising SEQ ID NO: 1 or a variant or a portion thereof. This isolated DNA molecule, or variant or portion thereof may be used to synthesize a protein having SEQ ID NO: 5, 7, 8 or 9. As the SNP at position 38 in SEQ ID NO: 1 is upstream of the coding region, both the A variant and the T variant of nucleotide 38 of SEQ ID NO: 1 may be used to make these proteins (e.g., the variation does not affect amino acid sequence). The isolated DNA molecule of SEQ ID NO: 1 may also be used as a control for genotyping Bos sp. animals.

In one aspect, the invention is an isolated DNA molecule comprising SEQ ID NO: 6 or a variant or portion thereof. This isolated DNA molecule or variant or portion thereof may be used to synthesize a protein having SEQ ID NO: 5, 7, 8 or 9.

The term "DNA molecule" generally refers to a strand of DNA or a derivative or mimic thereof, comprising at least one nucleotide base, such as, for example, a naturally occurring purine or pyrimidine base found in DNA (e.g., adenine "A", guanine "G" (or inosine "I), thymine "T" (or uracil "U"), and cytosine "C"). The term encompasses DNA molecules that are "oligonucleotides" and "polynucleotides". These definitions generally refer to a double-stranded molecule or at least one single-stranded molecule that comprises one or more complementary strand(s) or "complement(s)" of a particular sequence comprising a strand of the molecule.

An "isolated DNA molecule" is one that is separated from other nucleic acid molecules that are present in the natural source of the DNA molecule. An isolated DNA molecule may comprise transcribed nucleic acid(s), regulatory sequences, coding sequences, or the like, isolated substantially away from other such sequences, such as other naturally occurring nucleic acid molecules, regulatory sequences, polypeptide or peptide encoding sequences, etc.

"Variants" of DNA molecules have substantial identity to the sequences set forth in SEQ ID NO: 1 or SEQ ID NO: 6, including sequences having at least 70% sequence identity, preferably at least 75%, 80%, 85%, 90%, 95%, 96%, 97%, 98%, or 99% or higher sequence identity compared to a polynucleotide sequence of this invention using the methods described herein, (e.g., BLAST analysis, as described below).

Typically, a variant of a DNA molecule will contain one or more substitutions, additions, deletions and/or insertions, preferably such that the amino acid sequence of the polypeptide encoded by the variant DNA molecule is the same as that encoded by the DNA molecule sequences specifically set forth herein. It will be appreciated by those of ordinary skill in the art that, as a result of the degeneracy of the genetic code, there are many nucleotide sequences that may encode the same polypeptide. DNA molecules that vary due to differences in codon usage are specifically contemplated by the present invention. Thus, this invention includes any isolated DNA molecule, or variant or portion thereof that encodes a protein having SEQ ID NO: 5, 7, 8 or 9.

"Variants" of polypeptides and proteins have substantial identity to the sequences set forth in SEQ ID NO: 5 or 7 including sequences having at least 90% sequence identity, preferably at least 95%, 96%, 97%, 98%, or 99% or higher sequence identity compared to an amino acid sequence of this invention using the methods described herein, (e.g., BLAST analysis, as described below).

Preference is given to introducing conservative amino acid substitutions at one or more of the predicted nonessential amino acid residues in SEQ ID NO: 5 or 7. A "conservative amino acid substitution" replaces the amino acid residue in the sequence by an amino acid residue with a similar side chain. Families of amino acid residues with similar side chains have been defined in the art. These families comprise amino acids with basic side chains (e.g. lysine, arginine, histidine), acidic side chains (e.g. aspartic acid, glutamic acid), uncharged polar side chains (e.g. glycine, asparagine, glutamine, serine, threonine, tyrosine, cysteine), nonpolar side chains (e.g. alanine, valine, leucine, isoleucine, proline, phenylalanine, methionine, tryptophan), beta-branched side chains (e.g. threonine, valine, isoleucine) and aromatic side chains (e.g. tyrosine, phenylalanine, tryptophan, histidine). A predicted nonessential amino acid residue in SEQ ID NO: 5 or 7 is thus preferably replaced by another amino acid residue of the same side-chain family.

In additional embodiments, the present invention provides portions comprising various lengths of contiguous stretches of sequence identical to or complementary to one SEQ ID NO: 1 or SEQ ID NO: 6. For example, DNA molecules are provided by this invention that comprise at least about 10, 15, 20, 30, 40, 50, 75, 100, 150, 200, 300, 400, or 500 or more contiguous nucleotides of SEQ ID NO: 1 or SEQ ID NO: 6. Preferably, portions of SEQ ID NO: 1 or SEQ ID NO: 6 are portions that encode for a polypeptide having the amino acid sequence of SEQ ID NO: 5, 7, 8 or 9.

Percent sequence identity is calculated by determining the number of matched positions in aligned nucleic acid sequences, dividing the number of matched positions by the total number of aligned nucleotides, and multiplying by 100. A matched position refers to a position in which identical nucleotides occur at the same position in aligned nucleic acid sequences. Percent sequence identity also can be determined for any amino acid sequence. To determine percent sequence identity, a target nucleic acid or amino acid sequence is compared to the identified nucleic acid or amino acid sequence using the BLAST 2 Sequences (B12seq) program from the stand-alone version of BLASTZ containing BLASTN version 2.0.14 and BLASTP version 2.0.14. This stand-alone version of BLASTZ can be obtained on the U.S. government's National Center for Biotechnology Information web site (ncbi.nlm.nih.gov). Instructions explaining how to use the B12seq program can be found in the readme file accompanying BLASTZ.

B12seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to −1; -r is set to 2; and all other options are left at their default setting. The following command will generate an output file containing a comparison between two sequences: C:\B12seq -i c:\seq1.txt -j c:\seq2.txt -p blastn -o c:\output.txt -q -1 -r 2. If the target sequence shares homology with any portion of the identified sequence, then the designated output file will present those regions of homology as aligned sequences. If the target sequence does not share homology with any portion of the identified sequence, then the designated output file will not present aligned sequences.

Once aligned, a length is determined by counting the number of consecutive nucleotides from the target sequence presented in alignment with sequence from the identified sequence starting with any matched position and ending with any other matched position. A matched position is any position where an identical nucleotide is presented in both the target and identified sequence. Gaps presented in the target sequence are not counted since gaps are not nucleotides. Likewise, gaps presented in the identified sequence are not counted since target sequence nucleotides are counted, not nucleotides from the identified sequence. The percent identity over a particular length is determined by counting the number of matched positions over that length followed by multiplying the resulting value by 100.

The DNA molecules may be part of recombinantly engineered constructs designed to expresses the DNA molecule, either as an RNA molecule or also as a polypeptide. In certain embodiments, expression constructs are transiently present in a cell, while in other embodiments, they are stably integrated into a cellular genome.

Methods well known to those skilled in the art may be used to construct expression vectors containing the DNA molecules of interest and appropriate transcriptional and translational control elements. These methods include in vitro recombinant DNA techniques, synthetic techniques, and in vivo genetic recombination. In one embodiment, expression constructs of the invention comprise polynucleotide sequences comprising all or a variant or a portion of SEQ ID NO: 1 or SEQ ID NO: 6, to generate polypeptides that comprise all or a portion or a variant of SEQ ID NO: 5, 7, 8 or 9.

Regulatory sequences present in an expression vector include those non-translated regions of the vector, e.g., enhancers, promoters, 5' and 3' untranslated regions, repressors, activators, and such which interact with host cellular proteins to carry out transcription and translation. Such elements may vary in their strength and specificity. Depending on the vector system and cell utilized, any number of suitable transcription and translation elements, including constitutive and inducible promoters, may be used. Expression vectors may also include sequences encoding polypeptides that will assist in the purification or identification of the polypeptide product made using the expression system.

A useful prokaryotic expression system is the pET Expression System 30 (Novagen®). This bacterial plasmid system contains the pBR322 origin of replication and relies on bacteriophage T7 polymerase for expression of cloned products. Host strains such as C41 and BL21 have bacteriophage T7 polymerase cloned into their chromosome. Expression of T7 pol is regulated by the lac system. Without the presence of IPTG for induction, the lac repressor is bound to the operator and no transcription occurs. IPTG titrates the lac repressor and allows expression of T7 pol, which then expresses the protein of interest on the plasmid. Kanamycin resistance is included for screening.

A useful eukaryotic expression system the pCI-neo Mammalian Expression Vector (Promega®), which carries the human cytomegalovirus (CMV) immediate-early enhancer/promoter region to promote constitutive expression of cloned DNA inserts in mammalian cells. This vector also contains the neomycin phosphotransferase gene, a selectable marker for mammalian cells. The pCI-neo Vector can be used for transient or stable expression by selecting transfected cells with the antibiotic G-418.

DEFINITIONS

Unless defined otherwise, technical and scientific terms used herein have the same meaning as commonly understood by one of ordinary skill in the art to which this invention belongs. For purposes of the present invention, the following terms are defined below.

The term "locus" (plural loci) as used herein is a fixed position on a chromosome, and may or may not be occupied by one or more genes.

The term "allele" as used herein is a variant of the DNA sequence at a given locus.

The term "gene" is a functional protein, polypeptide, peptide-encoding unit, as well as non-transcribed DNA sequences involved in the regulation of expression. As will be understood by those in the art, this functional term includes genomic sequences, cDNA sequences, and smaller engineered gene segments that express, or is adapted to express, proteins, polypeptides, domains, peptides, fusion proteins, and mutants. As used herein, the term "PMCH gene" includes all of the sequence reproduced in SEQ ID NO: 1.

The term "genotype" or "genotypic" refers to the genetic constitution of an animal, for example, the alleles present at one or more specific loci. As used herein, the term "genotyping" refers to the process that is used to determine the animal's genotype.

The term "polymorphism" refers to the presence in a population of two (or more) allelic variants. Such allelic variants include sequence variation in a single base, for example a single nucleotide polymorphism (SNP).

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Materials and Methods

Animal Populations

The Canadian Beef Reference Herd (CBRH) was created using multiple ovulation and embryo transfer (MOET) and consisted of 17 full-sib families, 5 of which were purebred while the remainder were crossbred (Schmutz et al. 2001). The families ranged from 2 to 17 offspring, for a total of 136 calves. The 13 dams and 5 sires were purebred and included Charolais, Angus, Belgian Blue, Hereford, and Simmental breeds.

The Behaviour Population consisted of 382 feedlot steers used initially in a study of stress and behavioural parameters (Pugh 2007). These steers were purchased as commercial commercial stock in five lots from auction and therefore were predominantly crossbred. Behavioural measurements were applied equally to all animals, and all animals were on the same diet.

An additional population of purebred bulls was used to determine allele frequencies in Simmental, Charolais, Angus, and Hereford cattle Genomic DNA from six *Bos indicus* sires was also obtained in order to identify potential genetic differences between *Bos indicus* and *Bos taurus* PMCH.

DNA Extraction and cDNA Synthesis

CBRH and *Bos indicus* DNA Extraction (Schmutz et al. 1995)

From Semen: One straw of semen was thawed to room temperature and emptied into a 10 ml tube. It was then washed with 1×SSC and 10 mM EDTA, followed by centrifugation at 3000 rpm for 3 min, three to four times. The supernatant was removed from the sample, and the pellet was resuspended in 500 μl of 1× TE. Six μl of proteinase K (20 mg/ml) and 10 μl of 20% SDS were added and incubated for 1 h at 60° C. After the incubation period the tube was filled with 1×SSC with 10 mM EDTA and centrifuged at 12,000 rpm for 3 min. The supernatent was removed from the pellet, and 40 μl of proteinase K and 450 μl of semen extraction buffer were added (100 mM Tris-HCl pH 8.3, 10 mM EDTA, 500 mM NaCl, 1% SDS, and 2% mercaptoethanol). This solution was then incubated at 60° C. overnight. The following morning, 20 μl of proteinase K (20 mg/ml) was added, and the solution was incubated overnight again. Phenol/chloroform extraction and ethanol precipitation were then performed. The DNA pellet was stored at 4° C. until needed for PCR.

*CBRH and Behaviour Population DNA extraction* (Montgomery & Sise 1990):

White blood cells were collected from whole blood following lysis of the red blood cells in 2.5 volumes of cold sterile lysing solution (150 mM NH4Cl, 10 mM KCl, and 0.1 mM EDTA). The solutions were held on ice, and red blood lysis observed by a change in the color of the solution from blood red to a dark clear red, 2-10 min after the addition of the lysing solution. White cells were then harvested by spinning at a relative centrifugal force (RCF) of 2000 for 10 min at 4° C. Pelleted white cells were resuspended with a pasteur pipette and washed twice in 10 ml of Tris buffered saline (140 mM NaCl, 0.5 mM KCl, 0.25 mM Tris HCl pH 7.4). Cells were pelleted between washes in a bench-top centrifuge spun at an approximate RCF of 1000 for 3 min.

Washed white blood cells were completely resuspended by vigorous vortexing in 9 ml of TE (0.1 mM EDTA, 10 mM Tris-HCl pH 8.0) so that no cell clumps remained. Fifty μl of proteinase K (10 mg/ml) and 0.5 ml 0.5 M EDTA, pH 8.0 were added and the tubes mixed. Five hundred μl of 10% SDS was added while gently swirling the tubes. The tubes were then incubated at 50° C. in a water bath with occasional mixing for 3 h. Following proteinase K digestion, 4.3 ml of a saturated NaCl solution was added, the tubes were shaken vigorously for 30 s, and spun at RCF 2000 for 10 min. The supernatant containing DNA was transferred to a clean glass tube and two volumes of 95% ethanol were added. The DNA was spooled out using a sealed pasteur pipette and washed in 70% ethanol. The DNA was dried and resuspended in 200-

400 µl of TE. The tubes containing DNA in TE were placed on a mixing wheel in a cold room for at least 24 h to ensure resuspension was complete. The concentration of DNA was measured in a scanning spectrophotometer.

*Purebred Bull DNA Extraction* (Fitzsimmons et al. 1998)

DNA was obtained from whole blood via a phenol/chloroform extraction performed on an Automated Applied Biosystems 340A Nucleic Acid Extractor. Blood from both the CBRH and the Behaviour Population had been collected in EDTA and was extracted using a salt extraction method (Montgomery & Sise 1990). Genomic DNA from the purebred bull population had been extracted using a phenol/chloroform method, as described by Fitzsimmons et al. (1998). Genomic DNA extraction from semen of the *Bos indicus* animals followed the same methodology used to extract DNA from semen for animals in the CBRH. Samples from assorted tissues were previously obtained from a 5 week-old Holstein calf, two Holstein-cross calves of less than 1 week old, and a 19 month-old crossbred *Bos taurus* steer. The tissue samples from the Holstein calf and the steer were immediately immersed in liquid nitrogen.

*Total RNA extraction and cDNA synthesis methods* (Goodall & Schmutz 2007).

Tissue sample collection: Fifteen tissues were collected from a 5-week-old Holstein bull calf and a 19-month-old crossbred *Bos taurus* steer immediately after death and snap frozen in liquid nitrogen. Each tissue was pulverized in an RNA-free area using a mortar and pestle for RNA extraction. Assorted tissues were collected from the Holstein-cross calves shortly following death and placed in RNAlater® (Ambion) for subsequent RNA extraction.

*Complementary DNA Synthesis* (Goodall and Schmutz 2007):

Total RNA was isolated from the biopsies and other tissue samples using total RNA isolation reagent (TRIzol: Gibco). A DNA digest was then performed and included approximately 4 ug of total RNA, 1 µl of 10× Reaction Buffer, and 1 µl of DNaseI (Gibco). The mixture was incubated at room temperature for 15 min. One µl of 25 mM EDTA was added and the mixture was incubated at 65° C. for 15 min then placed on ice for 1 min, following which the mixture was briefly centrifuged. Synthesis of cDNA was then performed. 1 µl of oligo(dT) primer (Gibco) was added and the mixture was incubated at 65° C. for 10 min and placed on ice for 1 min. Two µl of 10× RT buffer, 4 µl of 25 mM $MgCl_2$, 1 µl of 10 mM dNTPs, 2 µl of 0.1 mM DTT, and 1 µl of RNAseOUT™ (Invitrogen) were then added to the mixture and incubated at 42° C. for 2 min. One µl of SuperscriptII RT™ (Invitrogen) was added and incubated at 42° C. for 60 min. The reaction was the incubated at 70° C. for 15 min and chilled on ice. The mixture was then centrifuged briefly and 1 µl of RNase H (Invitrogen) was added, followed by incubation at 37° C. for 20 min. The mixture was then divided into 5 µl aliquots and stored either at 4° C. (for immediate use) or at −80° C. (for long-term storage). Each 5 µl aliquot was diluted with 30 µl of 1× TE (pH 8.0) before use as a template for PCR.

Synthesis of cDNA from total brain RNA of the steer, as well as from tissues obtained from the Holstein-cross calves was performed following a mixed protocol from Invitrogen (Burlington, Ont.) and Fermentas (Burlington, Ont.).

Genomic DNA PCR Reaction Conditions

Polymerase Chain Reaction (PCR) primers were designed based on available human (NM_002674), mouse (NM_029971), and predicted bovine (XM_584729) mRNA PMCH sequences, as well as from bovine genomic (NW_270499) sequence (NCBI 2005). Genomic DNA from five dams and five sires of the CBRH were used initially for Single Nucleotide Polymorphism (SNP) identification. Primers were designed to amplify the coding region, including the introns, of PMCH for an expected product of 1383 base pairs (bp). Additional primers were designed to amplify a portion of the upstream region of the gene for an expected product of 438 bp.

To amplify the coding region of PMCH, 25-50 ng of genomic DNA was added to each 14 µl reaction containing 0.2 mM dNTP, 2 mM MgCl2, 10 µmol of each primer (PMCH for (5'-GCAAACATCAAACTAAGGATGG-3') [SEQ ID NO: 10] and PMCHrev (5'-CGTATGGTTAGCATGT-TAAGC-3') [SEQ ID NO: 11]); 1×PCR buffer, 0.5 U of Taq Polymerase (Invitrogen), and 9.5 µl of deionized water ($dH_2O$). The reaction was carried out in a Stratagene® RobCycler® PCR machine. Initial denaturation was 4 min at 95° C., followed by 37 cycles of: denaturation for 50 s at 95° C., annealing for 50 s at 53° C., and extension at 72° C. for 1 min 30 s. The reaction concluded with a final extension for 4 min at 72° C. The PCR reaction cocktail for upstream region amplification was the same as for the coding region reaction with the exception of the substitution of 3 mM $MgCl_2$, and 9.2 µl of $dH_2O$. The amplification cycle was also the same, with the exception of a 50 s extension time. The primers used were PromFor (5'-GGTTGGTTTCTATCTGATGAG-3') [SEQ ID NO: 12] and Exon1rev (5'-GTCGCATTATCACTTAC-CTTTG-3') [SEQ ID NO: 13]. PCR products were analyzed on a 2% agarose gel with a 1 kb plus DNA ladder (Gibco).

Sequencing

Genomic DNA from five of the dams (Angus_2, Charolais_9, Charolais_11, Belgian Blue 19, and Simmental_23) as well as all five sires (Angus_4, Limousin_8, Charolais_12, Hereford_16, and Simmental_24) of the CBRH, as well as genomic DNA from the six *Bos indicus* sires, were amplified by PCR and sent for DNA sequencing.

PCR products were excised from the agarose gel and extracted following the protocol as outlined in the Gel Extraction Kit (Qiagen, Mississauga, Ont.). To quantify the products, 2 µl of each extracted product was then added to 5 µl of $dH_2O$ and 1.5 µl of Ficoll Loading buffer and run alongside a DNA mass ladder (Gibco) in a 1.5% agarose gel.

The extracted products were then sequenced on an Applied Biosystems Sequencer. Brain cDNA from the 19 month-old crossbred steer was also chosen for sequencing. In order to obtain sequence from the entire coding region, two reactions were carried out as a result of the presence of spurious products. The amplification of exons 1 and 2 used primers BrEx1 for (5'-CCTTGTTTGACTCTATGC-3') [SEQ ID NO: 14] and cDNArev (5'-GCATACACCTAAGCATGTCAAAATC-3') [SEQ ID NO: 15]. The amplification of exons 2 and 3 used primers cDNA for (5'-CAAAAATTCAAAGAATGCAGGT-TCC-3') [SEQ ID NO: 16] and BrEx3rev (5'-GACTTGC-CAACAAGGTCG-3') [SEQ ID NO: 17]. The conditions for both reactions were the same. The 15 µl reaction cocktail contained 5-8 ng of cDNA, 0.2 mM dNTP, 2.5 mM $MgCl_2$, 10 µmol of each primer, 1×PCR buffer, 0.5 U of Taq Polymerase (Fernentas), and 8.6 µl of dH2O. PCR amplification began with an initial denaturation at 95° C. for 4 min, followed by 35 cycles of 95° C. for 50 s, annealing at 56° C. for 50 s, and extension at 72° C. for 50 s. Amplification concluded with a 4 min final extension at 72° C. Products were analyzed on a 1.5% agarose gel with a 1 kb plus DNA ladder (Gibco). Extraction, quantification, and sequencing of the brain cDNA product were the same as for genomic DNA.

PCR-Restriction Fragment Length Polymorphism

A PCR-Restriction Fragment Length Polymorphism (RFLP) assay was designed to genotype the remaining CBRH dams and offspring, as well as the purebred bull and Behaviour populations at the −134 SNP. In order to identify the SNP allele, a mismatch primer Mm for (5'-GATGAGT-CATTTCTAAAATGACG-3') [SEQ ID NO: 18] was designed to introduce a TaiI digest site in the presence of the thymine allele, but absent in the adenosine allele. The reaction used the reverse primer Exon1rev. Digestion of the PCR product resulted in fragments of 21, 146, and 257 bp when the thymine allele was present, and fragments of 146 and 278 bp when the adenosine allele was present.

Each 15 µl reaction cocktail contained 25-50 ng of genomic DNA, 0.2 mM dNTP, 2 mM MgCl$_2$, 10 µmol of each primer, 1×PCR buffer, 0.5 U of Taq Polymerase (Invitrogen), and 9.5 µl of dH$_2$O. The PCR reaction began with a 4 min denaturation at 95° C., followed by 34 cycles of denaturation at 95° C. for 50 s, annealing at 53° C. for 50 s, and extension at 72° C. for 50 s, and finished with a 4 min final extension. 1 µl of TaiI I and 1.5 µl of Buffer R (Fermentas) were then added to each 15 µl PCR reaction and digested at 65° C. for 2.5-3 hours. The digest was then analyzed on a 4% DNA agar gel (Marine Bioproducts, Delta, B.C.).

Mapping

Once genotyping of the CBRH was completed, CRIMAP (Green et al. 1990) was used to analyze PMCH with previously genotyped microsatellites on BTA5 (Schmutz et al. 2001)

Tissue Expression Profile

A tissue expression profile was obtained by performing PCR on cDNA samples from assorted tissues (spleen, adrenal gland, thymus, kidney, liver, lymph node, lung, heart, brain, spinal cord, skeletal muscle, adipose, rumen, abomassum, abomassal muscle, large intestine, and small intestine) obtained from the 5 week-old Holstein calf and the Holstein-cross calves, as well as the 19 month old steer. Primers cDNA for and cDNArev were used. Each 15 µl reaction contained 5-8 ng of cDNA, 0.2 mM dNTP, 2.5 mM MgCl2, 10 µmol of each primer, 1×PCR buffer, 0.5 U of Taq Polymerase (Fermentas), and 8.6 µl of dH$_2$O.

Amplification was carried out as follows: denaturation at 95° C. for 4 min, 37 cycles of denaturation at 95° C. for 50 s, annealing at 59° C. for 50 s, and extension at 72° C. for 50 s and concluded with a final extension of 72° C. for 4 min. Products were analyzed on a 1.5% agarose gel with a 1 kb plus DNA ladder (Gibco). PCR for Glyceraldehyde-3-phosphate dehydrogenase (GAPDH) was performed on all samples as a positive control, using the same PCR conditions. The reaction used primers GAPDH for (5'-GTTTGTGATGGGCGT-GAAC-3') and GAPDHrev (5'-GTGGACAGTGGTCAT-AAGT-3').

Transcriptional Start Site Prediction

In order to predict the transcriptional start site of exon 1, the Bos taurus PMCH genomic sequence from Limousin 8 (accession number DQ499531, submitted) was analyzed using the Neural Network Promoter Prediction version 2.2 (1999) available online at http://fruitfly.org/seq_tools/promoter.html (Reese & Eeckman 1995). The program identifies transcriptional elements within the submitted eukaryotic promoter sequence and predicts the most likely transcriptional start site. Additionally, the cattle promoter region sequence obtained from sequencing was added to the alignment of human and rat PMCH promoter region sequence and transcriptional start site prediction as determined by Viale et al. (1997) for comparative purposes.

Computational Analysis of the Promoter Region

A preliminary analysis of promoter binding sites was conducted by submitting the 5' sequences of each allele to P-Match, part of the Biobase Biological Database (2006), which can be found at www.gene-regulation.com. P-Match searches for potential transcription factor binding sites in any sequence using the TRANSFAC® database. The first 173 nucleotides of the sequenced PMCH 5' region from Charolais_12 (A/A) as well as Simmental_24 (T/T) were submitted. The matrix group chosen was vertebrates, with the cut-off set to minimize false negatives.

Results

PCR primers were designed based on available human (NM_002674), mouse (NM_029971), and predicted bovine (XM_584729) PMCH mRNA sequences, as well as bovine genomic (NW_270499) sequence (NCBI 2005). Initially, dams and sires from the CBRH were used for SNP identification. Forward (PMCHfor) and reverse (PMCHrev) primers were designed to amplify the coding region of PMCH for an expected product of 1383-bp. A second set consisting of forward (PromFor) and reverse (Exon1rev) primers was designed to amplify the 5' untranslated region (UTR) which gave an expected product of 438-bp. The combined length of both amplified products was 1493 bp. The entire PCR product (1493 bp) from Limousin 8 of the CBRH (male, heterozygote) was submitted to GenBank (accession number DQ499531).

Sequencing results revealed the presence of an A-to-T SNP at position −134, relative to the translation start codon of the Bos taurus PMCH sequence [g.−134 A-to-T; FIG. 2]. Genomic DNA was additionally obtained from six Bos indicus sires and was sequences for comparative purposes. One of these animals was heterozygous at this SNP (g.−134AT), while the remaining five were homozygous g.−134AA.

An intronic A-to-C SNP had been previously identified in Bos taurus/Bos indicus cross cattle by Stone et al. (2002). This intronic SNP was observed in one Bos indicus sire sequenced (g.929AC). Four Bos indicus sires were g.929CC at this position and one was g.929CT, while all Bos taurus animals sequenced were g.929AA. One additional SNP, g.102 C-to-T in exon 1, was observed in one Bos indicus animal sequenced. This SNP did not alter the amino acid. The five remaining Bos indicus animals were g.102CC while all Bos taurus animals were g.102TT at this position. No other SNP's were observed in this study.

A PCR restriction fragment length polymorphism (RFLP) assay was designed to genotype the remaining CBRH offspring as well as the Behaviour population at the g.−134 A-to-T SNP. Allelic frequencies were determined in the CBRH and Behaviour populations (Table 1). A population of purebred Bos taurus bulls was used to determine the allelic frequencies in purebred cattle (Table 1).

TABLE 1

PMCH allele frequencies in the Bos taurus CBRH and Behaviour populations, as well as by breed in the purebred bulls.

| Population | n | frequency of g.-134A | frequency of g.-134T |
|---|---|---|---|
| CBRH | 122 | 0.68 | 0.32 |
| Behaviour | 382 | 0.67 | 0.33 |
| Purebred Bulls: | | | |
| Angus | 55 | 0.83 | 0.17 |
| Hereford | 21 | 0.64 | 0.36 |
| Charolais | 52 | 0.73 | 0.27 |
| Simmental | 18 | 0.42 | 0.58 |

Statistical analysis focused on carcass traits pertaining to fat production. Of the traits analysed, grade fat and average fat were found to be significantly affected by PMCH genotype in both populations. The Canadian Beef grading Agency defines grade fat as the fat depth in millimeters at the leanest point of fat cover on the fourth-quarter of the rib eye. Average fat depth is calculated as the average from three measurements when more detailed carcass assessments are required.

Statistical analysis of PMCH genotype effect on carcass traits in both populations was carried out using SAS statistical software version 9.1 (SAS Institute Inc., Cary, N.C., USA). The MIXED procedure was used to calculate a one-way analysis of variance (ANOVA) statistic and the least-squared means (LSM). The model used to determine the effect of PMCH genotype on trait was $Y_{ij} = \mu + PMCH_i + e_{ij}$ where $Y_{ij}$ was the observation of the dependent variable (carcass trait) for the $i^{th}$ animal, $\mu$ was the overall population mean of the dependent variable, $PMCH_i$ was the effect of genotype, and $e_{ij}$ was the random error term for each experimental unit. The model used to determine the effect of PMCH genotype in the CBRH included the random effect of sire, the fixed effects of PMCH genotype and animal gender and the interaction between genotype and gender. Sire was not treated as an explanatory variable because not all genotypes existed within each family. Information regarding the pedigrees of the steers in the Behaviour population was not available so the model included only the effect on genotype.

A trait was considered to be significantly affected by PMCH genotype when $P \leq 0.05$. The interaction between genotype and gender was not significant in the CBRH. The CBRH showed a significant association of PMCH genotype with average fat and grade fat, which was validated in the Behaviour population (Table 2). In the Behaviour population fat depth increased relative to the number of g.−134A alleles present.

PMCH has been mapped in a number of mammalian species. PMCH is located on human chromosome 12q23-q24 (Pedeutour et al. 1994) on mouse chromosome 10 (Kapfhamer & Burmeister 1994), and on cattle chromosome 5 (Stone et al. 2002). In this study, genotypes of the CBRH population were analysed with previously genotyped microsatellite markers on BTA5 (Schmutz et al. 2000) using Cri-Map (Green et al. 1990). The results obtained here agree with those obtained previously by Stone et al. (2002) and place PMCH approximately 71 cM from the centromere (FIG. 5). Casas et al. (2000) identified suggestive associations with backfat and Warner-Bratzler shear force in this region of BTA5, as well as evidence of an interaction between this region with myostatin (MSTN) on BTA2 (FIG. 5). Li et al. (2004) also identified QTL for backfat in this region using haplotype analysis in a commercial line of *Bos taurus* (FIG. 5).

Due to the proximity of other genes shown to affect fat levels in been cattle, it is possible that this PMCH SNP may not be directly responsible for the observed differences in grade and average fat depth, but may instead be in linkage disequilibrium with another causative gene. Insulin-like growth factor 1 (IGF1) has been mapped in close proximity to PMCH on BTA5 (Kappes et al. 1997) (FIG. 5) and preliminary evidence has suggested that a T-to-C SNP in the promoter region of IGF1 may affect 20-day post-weaning gain in Angus cattle segregating for an allele associated with low IGF1 expression (Ge et al. 2001).

The data obtained in this study indicate that cattle with an adenosine nucleotide at position −134 relative to the start

TABLE 2

Statistical results summarizing the effect of PMCH genotype on average fat and grade fat in the CBRH and the Behaviour populations.

| Population | Trait (mm) | ANOVA LSM * | | | P-value |
|---|---|---|---|---|---|
| | | g.-134TT | g.-134AT | g.-134AA | |
| CBRH | Average Fat | 7.0 +/− 1.44$^a$ | 10.4 +/− 1.21$^{ab}$ | 10.2 +/− 1.22$^b$ | 0.011 |
| CBRH | Grade Fat | 5.1 +/− 1.00$^a$ | 8.2 +/− 0.81$^b$ | 8.0 +/− 0.81$^b$ | 0.041 |
| Behaviour | Average Fat | 8.6 +/− 0.53$^a$ | 9.7 +/− 0.29$^{ab}$ | 10.1 +/− 0.27$^b$ | 0.047 |
| Behaviour | Grade Fat | 7.2 +/− 0.53$^a$ | 8.3 +/− 0.29$^{ab}$ | 8.6 +/− 0.27$^b$ | 0.046 |

LSM, least-squared means; Means with the same letter are not significantly different (P > 0.05).

The observed allele frequencies within breeds support a causative effect of the SNP on subcutaneous fat.

A significant association of genotype with scrotal circumference was also found in the bulls of the CBRH, but not with testicular weight (data not shown). This suggests that this variant may also influence gonadal fat. This trait was, of course, not available for the crossbred steer population. Further work to determine the effect of increased gonadal fat should be undertaken as excess fat deposition in the scrotum above and around the testicles has been associated with reduced fertility, possibly due to heat insulation of the testicles (Skinner 1981).

Continental breeds, including Charolais and Simmental, are thought to be leaner than their British (Angus and Hereford) counterparts. Gregory et al. (1994) found that Angus and Hereford cattle had greater fat depth on average than Simmental and Charolais cattle. This is presumably due to the early maturation of British cattle, allowing them to produce more fat at a younger age compared with that of Continental cattle. In this study, Angus cattle showed the highest frequency of the g.−134A allele while Simmental animals had a higher frequency of the g.−134T allele (Table 1).

translation codon of PMCH more readily lay down backfat than those harboring the thymine nucleotide at this position. Due to the location, it was possible that this PMCH SNP may alter a transcription factor binding site. A preliminary analysis of promoter binding sites was conducted by submitting the 5' sequences of each allele to P-Match, part of the Biobase GmbH Biological Database (2006), which can be found at http://www.gene-regulation.com. P-Match searches for potential transcription factor binding sites in any sequence using the TRANSFAC® database (Matys et al. 2003). Parameters were set to search for promoters affecting transcription in vertebrates. A binding site for a transcriptional repressor, E4 promoter binding protein (E4BP4) (also known as NFIL3), was discovered overlapping the SNP in the presence of the g.−134T allele but not in the presence of the g.−134A allele (FIG. 6).

E4BP4 is a member of the basic leucine zipper protein (bZIP) family of transcriptional repressors and is ubiquitously expressed (Cowell et al. 1992). E4BP4 is thought to play a role in the regulation of the mammalian circadian oscillatory mechanism, which is responsible for adaptations to daily environmental changes (Cowell 2002). E4BP4 mRNA levels have been observed to increase in response to glucocorticoids, and binding sites for E4BP4 have been observed in genes that are negatively regulated by glucocorticoids (Mitsui et al. 2001). These findings suggest a potential mechanism of action for the SNP. One could postulate that, in the presence of glucocorticoids, E4BP4 binds the PMCH promoter element and mistakenly inhibits transcription of the gene when the g.−134T allele is present but not when the g.−134A allele is present. This would lead to downregulation of PMCH in the presence of the g.−134T allele which is supported by the findings that animals with the g.−134T allele produce less fat.

The consensus binding site for E4BP4 is (G/A)T(G/T)A(C/T)GTAA(C/T) (Cowell et al. 1992). The sequence found in Bos taurus when the g.−134T allele is present matches the consensus binding site with the exception of the presence of a guanine at the 3' end instead of a cytosine or thymine (FIG. 6). This nucleotide does not appear to be essential for E4BP4 binding as E4BP4 has been shown to tolerate certain mismatches within the consensus sequence and successfully bind DNA. DNA sequence with the same 3' guanine substitution has been shown to bind E4BP4 (Lai & Ting 1999). These results indicate that E4BP4 would be expected to bind cattle DNA when the g.−134T allele is present despite the presence of the guanine residue at the 3' end.

A sequence matching the E4BP4 consensus binding site appears to be absent in both rats and humans (Viale et al. 1997) (FIG. 6). Examination of this gene region in humans and rats indicates that the cattle PMCH g.−134T allele in Bos taurus cattle is likely to be the variant allele as an adenosine is typically present at this position in other species.

Sequencing and Single-Nucleotide Polymorphism Detection

The results of sequencing indicated an adenosine-to-thymine (A-to-T) SNP was present in the 5' untranslated region (UTR) of PMCH at position −134 relative to the start codon in the heterozygous state in 3 of the animals sequenced. Three other animals were homozygous for the T allele, while the remaining 4 animals were homozygous for the A allele. The complete genomic sequence from the sire Limousin 8 (heterozygote) from the CBRH was submitted to GenBank (accession number DQ499531) (FIG. 1). A brain sample from a 19 month-old crossbred steer was used to prepare copy-DNA (cDNA). The cDNA was also sequenced and submitted to GenBank (accession number EF175214) (FIG. 2). The remaining animals of the CBRH, as well as the purebred bulls and Behaviour population, were genotyped by RFLP (FIG. 3).

Human PMCH cDNA was found to be 66% identical to cattle, mouse cDNA was 62% identical, and rat cDNA was 59% identical. Translation of the cDNA sequence indicated that Bos taurus PMCH amino acid (aa) sequence is very similar to that of human, mouse, and rat. The cattle PMCH aa sequence was 91.5% similar to that of human, 83.0% similar to that of mouse, and 78.2% similar to that of rat (FIG. 4). Cattle NGE was found to differ from human, rat, and mouse by one amino acid at the $10^{th}$ position. Mouse sequence also had an additional amino acid substitution at position 13 that is distinct from human, rat, and cattle. NEI and MCH amino acid sequences were perfectly conserved in all four species.

Allele Frequency

The frequency of alleles was determined in the CBRH and Behaviour populations because this is an indication of the usefulness of the SNP for genetic testing. A breakdown of allele frequency by breed was determined using the purebred bulls (Table 1).

PMCH Maps to BTA5

PMCH had been previously mapped to bovine chromosome 5 (BTA5) (Stone et al. 2002) using an intronic SNP identified in Bos taurus/Bos indicus crossbred cattle. This intronic SNP was not observed in any of the Bos taurus animals sequenced in this study. Cattle from the CBRH were genotyped at the 5' UTR A-to-T SNP. Using multipoint linkage analysis of microsatellite alleles available from a previous study, and CRIMAP analysis (Green et al. 1990), PMCH was localized on BTA5 (FIG. 5). A log of the odds ratio (LOD) score of 3.23 was obtained between PMCH and BL37, of 4.85 with MAF23, and 6.54 with BMS1819. PMCH is 6.8 cM from BM1819, 13.7 cM from MAF23 and 23.7 cM from BL37 on BTA5.

Tissue Expression Profile

PMCH expression was present in most tissues examined from the 5 week-old Holstein calf including the spleen, adrenal gland, thymus, kidney, lymph node, brain, and spinal cord. PMCH expression was not observed in the lung, heart, abomassum, or small intestine. GAPDH expression was observed in all tissues examined.

Statistical Results

CBRH Population

Significant associations of PMCH were observed with carcass fat, as well as with shear force data and consumer taste panel evaluations. The Warner-Bratzler Shear Force value was developed by Bratzler in 1932 and is a quantitative measurement of the tenderness of cooked meat, where higher force measurements indicate tougher cuts of meat. The process involves drawing a flat blade through a specified size of cubed meat which rests in a triangular hole between two fixed plates. The amount of force necessary to draw the blade through the sample is the shear force score. The muscle fibers must run perpendicular to the blade path, and each sample is of a fixed cross-sectional area.

Palatability and tenderness are consumer taste panel traits. Initial tenderness was evaluated as the perceived tenderness of the first bite, using the front incisors to bite perpendicularly through the muscle grain. Overall tenderness was defined as the tenderness of the entire cube of meat, chewed with the molars just prior to being swallowed. The panelists were instructed to give numerical scores ranging from 1-9, with 1 being tough and 9 being tender. Palatability was defined as the overall experience of the meat, including flavor, juiciness, and tenderness and ranged from 1 (not palatable) to 9 (very palatable).

Carcass traits including average fat, grade fat, hip roast, shoulder roast, and steak shear force indicated significant associations ($P<0.05$) or trends ($1>P>0.05$) with PMCH genotype in the CBRH (Table 3).

TABLE 3

Least Squared Means (LSM) and P-values of carcass traits significantly associated with PMCH genotype in CBRH.

| Trait | ANOVA LSM* | | | P-value |
|---|---|---|---|---|
| | g.-134TT<br>n = 20 | g.-134AT<br>n = 39 | g.-134AA<br>n = 63 | |
| Average Fat (mm) | 7.0 +/- 1.44$^a$ | 10.4 +/- 1.21$^{ab}$ | 10.2 +/- 1.22$^b$ | 0.011 |
| Grade Fat (mm) | 5.7 +/- 1.00$^a$ | 8.2 +/- 0.81$^b$ | 8.0 +/- 0.81$^b$ | 0.041 |
| Hip Roast (AB) | 6.454 +/- 0.2776$^a$ | 7.121 +/- 0.1988$^{ab}$ | 7.221 +/- 0.1564$^b$ | 0.056 |
| Shoulder Roast (SK) | 8.101 +/- 0.2886$^{ab}$ | 8.314 +/- 0.2067$^b$ | 7.376 +/- 0.1626$^a$ | 0.001 |
| Steak Shear Force (SK) | 10.574 +/- 0.5020$^b$ | 10.187 +/- 0.3595$^b$ | 8.049 +/- 0.2828$^a$ | <.0001 |
| Steak Shear Force (AB) | 7.660 +/- 0.4880$^{ab}$ | 7.675 +/- 0.3406$^b$ | 6.413 +/- 0.2680$^a$ | 0.006 |
| Palatability | 4.2 +/- 0.22$^a$ | 4.5 +/- 0.16$^{ab}$ | 4.9 +/- 0.12$^b$ | 0.006 |
| Tenderness (Initial) | 4.7 +/- 0.30$^a$ | 5.3 +/- 0.21$^{ab}$ | 5.8 +/- 0.17$^b$ | 0.007 |
| Tenderness (Overall) | 4.6 +/- 0.30$^a$ | 5.3 +/- 0.21$^{ab}$ | 5.8 +/- 0.17$^b$ | 0.001 |

*Means with the same letter are not significantly different (P > 0.05).
The steaks were cooked to well-done at AB (Alberta) testing facility.
The steaks were cooked to medium at SK (Saskatchewan) testing facility.

Thymine homozygotes tended to have higher shear force values, indicating that cuts of meat from these animals were less tender than cuts from the adenosine homozygotes. The only exception was that of the hip roast measurement where thymine homozygotes were most tender. Additionally tenderness and palatability, as evaluated by a consumer taste panel, were found to have a significant association with PMCH genotype where the adenosine homozygotes were found to be most tender and palatable.

Behaviour Population

The Behaviour population, chosen as typical of a feedlot population, also showed a significant effect of PMCH genotype on average fat and grade fat (Table 4).

TABLE 4

Least Squared Means (LSM) and P-value for carcass traits significantly associated with PMCH genotype in the Behaviour population.

| Trait | ANOVA LSM* | | | P-value |
|---|---|---|---|---|
| | g.-134TT<br>n = 47 | g.-134AT<br>n = 155 | g.-134AA<br>n = 180 | |
| Average Fat (mm) | 8.6 +/- 0.53$^a$ | 9.7 +/- 0.29$^{ab}$ | 10.1 +/- 0.27$^b$ | 0.047 |
| Grade Fat (mm) | 7.2 +/- 0.53$^a$ | 8.3 +/- 0.29$^{ab}$ | 8.6 +/- 0.27$^b$ | 0.046 |

*Means with the same letter are not significantly different (P > 0.05).

Both traits showed an additive relationship with PMCH genotype in which the adenosine homozygotes had the highest levels of subcutaneous fat deposits. Meat quality traits including shear force values and consumer taste panel evaluations were not available for this population.

PMCH Exon 1 Start Site and Promoter Region Analysis

The results of transcription start site prediction analysis by the Neural Network Promoter Prediction version 2.2 algorithm (NNPP) on genomic sequence obtained from Limousin-8 (accession number DQ499531) provided four possible transcriptional start sites. The first prediction concerning the transcriptional start site was at nucleotide 103 of the submitted sequence, which would place the transcriptional start site 28 bp downstream of the predicted TATA Box. Based on the comparison of this predicted start site with the other three predictions made by NNPP, it appeared as though this prediction was the most likely to be correct. The three other predictions indicated the start sites at positions 317, 399, and 689 nucleotides of the submitted cattle sequence respectively, which would exclude portions of the known coding sequence. Additionally, the first prediction by NNPP also agreed with the predictions made by others concerning the rat and human exon 1 start site (Viale et al. 1997). The use of TATA box sequences and the exon 1 start site in the human and rat PMCH sequences as anchors, as well as the output from NNPP, allowed the start site of Bos taurus to be putatively placed 103 bp downstream from the beginning of the sequenced cattle gene, 28 bp downstream of the predicted TATA box (FIG. 6).

The results of P-match analysis on the cattle PMCH promoter region indicated the presence of a binding site for a transcriptional repressor, E4 promoter binding protein (E4BP4), in the presence of the g.-134T allele (Simmental 24) on the (+) DNA strand. The core similarity score, representing the similarity of the submitted sequence to the five most conserved nucleotides in the consensus transcription factor binding site, was a perfect 1.0. The matrix score, representing overall similarity between the consensus transcription factor binding site and the submitted sequence was 0.993. This binding site was not identified by P-match in the presence of the adenosine allele (Charolais 12). The consensus binding site for E4BP4 is (G/A)T(G/T)A(C/T)GTAA(C/T) (Cowell et al. 1992). The Bos taurus PMCH SNP is located at the $7^{th}$ position of this consensus sequence. The cattle sequence, when the thymine allele is present, is ATGATG-TAAG (FIG. 6), which matches the E4BP4 consensus binding site with the exception of the presence of a guanine at the 3' end instead of a cytosine or thymine. A sequence matching the E4BP4 consensus sequence appears to be absent in both rats and humans as they both contain an adenosine residue at position 7. Human sequence also contains an inserted adenosine at the $10^{th}$ position within the putative E4BP4 consensus sequence. Rat sequence bears very little similarity to the putative E4BP4 consensus sequence as rats have additional adenosine residues at positions 2, 5, 6, and 9 (FIG. 6).

REFERENCES

Baker, B. I. (1994) Melanin-concentrating hormone updated: Functional considerations, *Trends in Endocrinology and Metabolism* 5, 120-126.

Barth, A. D., Cates, W. F., & Harland, R. J. (1995) The effect of amount of body fat and loss of fat on breeding soundness classification of beef bulls. *Canadian Veterinary Journal* 36, 758-764.

Biobase GmBH (2006) available at: http://www.gene-regulation.com. Accessed 23 Aug., 2007.

Buchanan, F. C., Fitzsimmons, C. J., Van Kessel, A. G., Thue, T. D., Winkelman-Sim, D. C., & Schmutz, S. M. (2002) Association of a missense mutation in the bovine leptin gene with carcass fat content and leptin mRNA levels. *Genetics Selection Evolution* 34, 105-116.

Casas, E., Stone, R. T., Keele, J. W., Shackelford, S. D., Kappes, S. M., & Koohmaraie, M. (2000) Quantitative trait loci affecting growth and carcass composition of cattle segregating alternative forms of myostatin. *Journal of Animal Science* 78, 560-569.

Cowell, E. G., Skinner, A., & Hurst, H. C. (1992) Transcriptional Repression by a novel member of the bZIP family of transcription factors. *Molecular and Cellular Biology* 12, 3070-3077.

Cowell, I. G. (2002) E4BP4/NFIL3, a PAR-related bZIP factor with many roles. *BioEssays* 24, 1023-1029.

Gavrila, A., Chan, J. L., Miller, L. C., Heist, K., Yiannakouris, N., & Mantzoros, C. S. (2005) Circulating melanin-concentrating hormone, agouti-related protein, and α-melanin-stimulating hormone levels in relation to body composition: Alterations in response to food deprivation and recombinant human leptin administration. *The Journal of Clinical Endocrinology and Metabolism* 90, 1047-1054.

Ge W., Davis, M. E., Hines H. C., Irvin K. M. & Simmen R. C. M. (2001) Association of a genetic marker with blood serum insulin-like growth factor-I concentration and growth traits in Angus cattle. *Journal of Animal Science* 79, 1757-62.

Green, P., Falls, K., & Crooks, S (1990) *Documentation for CRI-MAP*. (St. Louis: Washington University School of Medicine).

Gregory, K. E., Cundiff, L. V., Koch, R. M., Dikeman, M. E., & Koohmaraie, M. (1994) Breed effects and retained heterosis for growth, carcass, and meat traits in advanced generations of composite populations of beef cattle. *Journal of Animal Science* 72, 833-850.

Ito, M., Gomori, A., Ishihara, A., Oda, Z., Mashiko, S., Matsushita, H., Yumoto, M., Ito, M., Sano, H., Tokita, S., Moriya, M., Iwaasa, H., & Kanatani, A., (2003) Characterization of MCH-mediated obesity in mice. *American Journal of Physiology, Endocrinology, and Metabolism* 284, E940-E945.

Kapfhamer, D. & Burmeister, M. (1994) Genetic map of the region around grizzled (gr) and mocha (mh) on mouse chromosome 10, homologous to human 19p13.3. *Genomics* 23, 635-642.

Kappes S. M., Keele J. W., Stone R. T., McGraw R. A., Sonstegard T. S., Smith T. P. L., Lopez-Corrales N. L. & Beattie C. W. (1997) A second-generation linkage map of the bovine genome. *Genome Research* 7, 235-49.

Lai C. K. & Ting L. P. (1999) Transcriptional repression of human hepatitis B virus genes by a bZIP family member, E4BP4. *Journal of Virology* 73, 3197-209.

Li, C., Basarab, J., Snelling, W. M., Benkel, B., Kneeland, J., Murdoch, B., Hansen, C., & Moore, S. S. (2004) Identification and fine mapping of quantitative trait loci for backfat on bovine chromosomes 2, 5, 6, 19, 21, and 23 in a commercial line of Bos taurus. *Journal of Animal Science* 82, 967-972.

Ludwig, D. S., Tritos, N. A., Mastaitis, J. W., Kulkarni, R., Kokkotou, E., Elmquist, J., Lowell, B., Flier, J. S., & Maratos-Flier E. (2001) Melanin-concentrating hormone overexpression in transgenic mice leads to obesity and insulin resistance. *The Journal of Clinical Investigation* 107, 379-386.

Matys V., Fricke E., Geffers R. et al. (2003) TRANSFAC: transcriptional regulation, from patterns to profiles. *Nucleic Acids Research* 31, 374-378.

Mitsui, S., Yamaguchi, S., Matsuo, T., Ishida, Y., & Okamura, H. (2001) Antagonistic role of E4BP4 and PAR proteins in the circadian oscillatory mechanism. *Genes and Development* 15, 995-1006.

Montgomery, J. A. & Sise, J. A. (1990) Extraction of DNA from sheep white blood cells. *New Zealand Journal of Agricultural Research* 33, 437-441

Nahon, J.-L., Presse, F., Bittencourt, J. C., Sawchenko, P. E., & Vale, W. (1989) The rat melanin-concentrating hormone messenger ribonucleic acid encodes multiple putative neuropeptides coexpressed in the dorsolateral hypothalamus. *Endocrinology* 125, 2056-2065.

Pedeutour F., Szpirer C. & Nahon J.-L. (1994) Assignment of the human pro-melanin-concentrating hormone gene (PMCH) to chromosome 12q23-q24 and two variant genes (PMCHL1 and PMCHL2) to Chromosome 5p14 and 5q12-q13. *Genomics* 19, 31-7.

Pissios, P., Bradley, R. L., & Maratos-Flier, E. (2006) Expanding the scales: The multiple roles of MCH in regulating energy balance and other biological functions. *Endocrine Reviews* 27, 606-620.

Pugh K. (2007) *An evaluation of the corticotrophin-releasing hormone and leptin gene SNPs relative to cattle behaviour*. MSc Thesis, University of Saskatchewan.

Reese, M. G. & Eeckman, F. H. (1995) New neural network algorithms for improved eukaryotic promoter site recognition. Genome Science and Technology 1, 45. Proceedings of the seventh international genome sequencing and analysis conference.

Schenkel, F. S., Miller, S. P., Ye, X., Moore, S. S., Nkrumah, J. D., Li, C., Yu, J., Mandell, I. B., Wilton, J. W., & Williams, J. L. (2005) Association of single nucleotide polymorphisms in the leptin gene with carcass and meat quality traits of beef cattle. *Journal of Animal Science* 83, 2009-2020.

Schmutz, S. M., Marquess, F. L., Berryere, T. G., & Moker, J. S. (1995) DNA marker-assisted selection of the polled condition in charolais cattle. *Mammalian Genome* 6, 710-713.

Schmutz, S. M., Buchanan, F. C., Winkelman-Sim, D. C., Pawlyshyn, V., Plante, Y., McKinnon, J. J., & Fournier, B. P. (2001) Development of the Canadian beef reference herd for gene mapping studies. *Theriogenology* 55, 963-972.

Shimada, M., Tritos, N. A., Lowell, B., Flier, J. S., & Maratos-Flier, E. (1998) Mice lacking melanin-concentrating hormone are hypophagic and lean *Nature* 396, 670-674.

Skinner, J. D. (1981) Nutrition and fertility in pedigree bulls. In: *Environmental factors in mammal reproduction* (ed. by D. Gilmore & B. Cook), pp. 160-8. Macmillan, London.

Stone, R. T., Grosse, W. M., Casas, E., Smith, T. P. L., Kelle, J. W., and Bennett, G. L. (2002) Use of bovine EST data and human genomic sequences to map 100 gene-specific bovine markers. *Mammalian Genome* 13, 211-215.

Viale, A., Zhixing, Y., Breton, C., Pedeutour, F., Coquerel, A., Jordan, D., & Nahon, J-L. (1997) The melanin-concentrating hormone gene in human: Flanking region analysis, fine chromosome mapping, and tissue-specific expression. *Molecular Brain Research* 46, 243-255.

The invention claimed is:

1. A method of identifying a *Bos* sp, animal likely to have a phenotype of higher grade fat depth and higher average fat depth, lower shear force and improved palatability, comprising:
   (a) isolating a nucleic acid sample from the animal, and
   (b) determining, by direct detection of the nucleotides present at position 38 in SEQ ID NO: 1, whether the genotype at position 38 in SEQ ID NO: 1, in the nucleic acid sample, is "AA", "TT" or "AT",
   (c) identifying an animal with the "AA" or "AT" genotype as likely to have the phenotype or identifying an animal with the "TT" genotype as not likely to have the phenotype.

2. The method of claim 1, wherein the nucleic acid sample is a DNA sample.

3. The method of claim 1, wherein step (b) is performed by amplifying a region of the nucleic acid sample using an oligonucleotide primer pair, to form nucleic acid amplification products comprising the nucleotide at position 38 in SEQ ID NO: 1.

4. The method of claim 2, wherein step (b) is performed by amplifying a region of the DNA sample using an oligonucleotide primer pair, to form nucleic acid amplification products comprising the nucleotide at position 38 in SEQ ID NO: 1.

5. The method of claim 3 wherein at least one primer of the oligonucleotide pair comprises at least 10 contiguous nucleotides of the nucleic acid sequence of SEQ ID NO: 1 or a complement thereof.

6. The method of claim 4 wherein at least one primer of the oligonucleotide pair comprises at least 10 contiguous nucleotides of the nucleic acid sequence of SEQ ID NO: 1 or a complement thereof.

7. The method of claim 5, wherein PCR amplification is performed using a primer having SEQ ID NO: 18 and a primer having SEQ ID NO: 13 and the nucleic acid amplification products are analysed by digestion with restriction endonuclease TaiI.

8. The method of claim 6, wherein PCR amplification is performed using a primer having SEQ ID NO: 18 and a primer having SEQ ID NO: 13 and the DNA amplification products are analysed by digestion with restriction endonuclease TaiI.

9. A method of regulating the time to finishing, in a group of *Bos* sp, animals entering a feedlot, said method comprising:
   (a) determining, by direct detection of the nucleotides present at position 38 in SEQ ID NO: 1, whether the animals in the group have an "AA", "AT" or "TT" genotype at position 38 in SEQ ID NO: 1,
   (b) providing each animal in the group a diet that is selected according to its genotype at position 38 in SEQ ID NO: 1, and
   (c) feeding animals of the same genotype the same diet.

10. The method of claim 9 wherein at step (b) the diet selected for each animal also selected according to its phenotype on entering the feedlot.

11. The method of claim 9, wherein the animals in the group finish either:
   (a) at the same selected time with approximately the same grade fat depth and average fat depth, or
   (b) at different selected times with approximately the same grade fat depth and average fat depth.

12. A method of improving the quality and consistency of the average fat depth and grade fat depth of carcasses obtained from a group of *Bos* sp, animals from a feedlot, or the quality and consistency of the shear force and palatability of beef obtained from these animals, said method comprising:
   (a) genotyping the animals in the group, by direct detection of the nucleotides present at position 38 in SEQ ID NO: 1, to determine whether they have an "AA", "AT" or "TT" genotype at position 38 in SEQ ID NO: 1,
   (b) sorting the animals into sub-groups according to their genotype at position 38 in SEQ ID NO: 1, and
   (c) feeding the animals in any one sub-group the same diet for the same length of time.

13. The method of claim 12 wherein at step (b) the animals are sorted into sub-groups on the basis of their phenotype on entering the feedlot.

14. A method of breeding *Bos* sp, animals, based on the knowledge of the animals' genotype, comprising the steps of:
   (a) obtaining a nucleic acid sample from the animals;
   (b) analysing the nucleic acid sample to determine by direct detection of the nucleotides present at position 38 in SEQ ID NO: 1, the genotype at position 38 in SEQ ID NO: 1 in the animals, wherein the genotype will be one of "AA", "AT", or "TT" at this position,
   (c) selecting a first animal and a second animal for breeding, on the basis of their genotype at this position, and
   (d) breeding the first animal with the second animal.

15. The method of claim 14 wherein at step (c) the first animal and second animal are selected so as to produce offspring with a genotype selected from the group consisting of:
   (a) an "AA" genotype at position 38 in SEQ ID NO: 1;
   (b) an "AT" genotype at position 38 in SEQ ID NO: 1, and
   (c) a "TT" genotype at position 38 in SEQ ID NO: 1.

16. A method of increasing the grade fat depth and average fat depth, lowering the shear force and improving palatability, in a group of *Bos* sp, animals, comprising:
   (a) obtaining a nucleic acid sample from the animals;
   (b) analysing the nucleic acid sample to determine a genetic predisposition of *Bos* sp, animals to have higher average fat depth and higher grade fat depth, lower shear force and better palatability, by determining, by direct detection of the nucleotides present at position 38 in SEQ ID NO: 1, their genotype at position 38 in SEQ ID NO: 1,
   (c) selecting animals that have the "A" allele at position 38 in SEQ ID NO: 1 for inclusion in the group, and
   (d) removing animals that have only the "T" allele from the group.

* * * * *

SEQUENCE LISTING

<160> NUMBER OF SEQ ID NOS: 23

<210> SEQ ID NO 1
<211> LENGTH: 1493
<212> TYPE: DNA
<213> ORGANISM: Bos taurus
<220> FEATURE:
<221> NAME/KEY: misc_feature
<222> LOCATION: (38)..(38)
<223> OTHER INFORMATION: A or T at this position

<400> SEQUENCE: 1

```
gttggtttct atctgatgag tcatttctaa aatgatgnaa gttttcaag tgctttctat        60
tcaagctgga aaatatataa aggcaagaat catttacaaa gcaggatgac tgagaaattt       120
cacttcattt tatacatcct tgtttgactc tatgcaaaca tcaaactaag gatggcaaaa      180
atgagtttct cttcctacat attaatacta acttttcctt tgctttctca aggcatttca       240
ctttcagcat ccaagtcgat aagaaattta gatgatgaca tggtatttaa aacgttgagg       300
ctggggaaag cctttcagaa ggaagatacc gcagaaaaat caattgttgt tccttccctg       360
gagcaatata aaaatgatga gagcagtttc atgaatgatg aagaaaacaa aaattcaaag      420
gtaagtgata atgcgacttg tcctttattt caatggaaat ttgaatgatc tttatgaatc       480
ctttgaaagt aaagttgata cttttataag cagaagcacg tgaaaaaaag ttacagtatg       540
cattagaaca attaaacaaa tttcatacat accaggttgt tcttccattc tgggaaatat       600
ctcttattca aaaagttttt attccctgaa atcttgtat ctaaagtatt tcttaaaggg        660
taaaacagt gcagggcata tttaaattga tcaataagaa tattcacaa ttgtattata         720
gttccattcc aaatagaaca gttaaaacac aaatcaacct tttctttaca gaatgcaggt      780
tccaaacata atttcttaaa tcatggcctg ccactgaatc tggctataaa accttatctt       840
gcactaaaag gatctgtagc ttttccagct gagaatgaag ttcaaaatac tgaatcaaca       900
caagaaaaaa gagaaattgg ggatgaagaa aactcagcta aatttcctat aggaaggaga      960
gattttgaca gtgagtagtt ttttaaaat tgaattctta taccttaata tcataaaata       1020
gaactttgaa tttaatggaa tttgggtcca atcataacaa aatcaaacaa gaccatgatt      1080
caacttgtac ttgatactaa gtgactcttg caaaagatgt gaaattaaaa agtatttaat      1140
tagttattac aattgtaatt tactcagatt tagctatact agatccattc ttttatttct      1200
aatcaacttt gtgtgatact agtcttctaa acaattttgt ttttccttca gtgcttaggt      1260
gtatgctggg aagagtctat cgaccttgtt ggcaagtctg atgcctgttg gtccacatca      1320
tcatttaaaa agaaagcaaa atcatttaat tgcctctcgg gaaaaaagcc cttaatgttg      1380
ctatgacttg tattatttta aatgtctgtt ttaaaagaaa gtggtattgt tatgcctaaa      1440
tgattgcttt acttgtgcat taaactttat gaattttatg cataattatg act             1493
```

<210> SEQ ID NO 2
<211> LENGTH: 83
<212> TYPE: PRT
<213> ORGANISM: Bos taurus

<400> SEQUENCE: 2

```
Met Ala Lys Met Ser Phe Ser Ser Tyr Ile Leu Ile Leu Thr Phe Ser
 1               5                  10                  15

Leu Leu Ser Gln Gly Ile Ser Leu Ser Ala Ser Lys Ser Ile Arg Asn
            20                  25                  30
```

```
Leu Asp Asp Asp Met Val Phe Lys Thr Leu Arg Leu Gly Lys Ala Phe
         35                  40                  45

Gln Lys Glu Asp Thr Ala Glu Lys Ser Ile Val Val Pro Ser Leu Glu
 50                  55                  60

Gln Tyr Lys Asn Asp Glu Ser Ser Phe Met Asn Asp Glu Glu Asn Lys
 65                  70                  75                  80

Asn Ser Lys

<210> SEQ ID NO 3
<211> LENGTH: 66
<212> TYPE: PRT
<213> ORGANISM: Bos taurus

<400> SEQUENCE: 3

Asn Ala Gly Ser Lys His Asn Phe Leu Asn His Gly Leu Pro Leu Asn
 1               5                  10                  15

Leu Ala Ile Lys Pro Tyr Leu Ala Leu Lys Gly Ser Val Ala Phe Pro
             20                  25                  30

Ala Glu Asn Glu Val Gln Asn Thr Glu Ser Thr Gln Glu Lys Arg Glu
         35                  40                  45

Ile Gly Asp Glu Glu Asn Ser Ala Lys Phe Pro Ile Gly Arg Arg Asp
 50                  55                  60

Phe Asp
 65

<210> SEQ ID NO 4
<211> LENGTH: 16
<212> TYPE: PRT
<213> ORGANISM: Bos taurus

<400> SEQUENCE: 4

Met Leu Arg Cys Met Leu Gly Arg Val Tyr Arg Pro Cys Trp Gln Val
 1               5                  10                  15

<210> SEQ ID NO 5
<211> LENGTH: 165
<212> TYPE: PRT
<213> ORGANISM: Bos taurus

<400> SEQUENCE: 5

Met Ala Lys Met Ser Phe Ser Ser Tyr Ile Leu Ile Leu Thr Phe Ser
 1               5                  10                  15

Leu Leu Ser Gln Gly Ile Ser Leu Ser Ala Ser Lys Ser Ile Arg Asn
             20                  25                  30

Leu Asp Asp Asp Met Val Phe Lys Thr Leu Arg Leu Gly Lys Ala Phe
         35                  40                  45

Gln Lys Glu Asp Thr Ala Glu Lys Ser Ile Val Val Pro Ser Leu Glu
 50                  55                  60

Gln Tyr Lys Asn Asp Glu Ser Ser Phe Met Asn Asp Glu Glu Asn Lys
 65                  70                  75                  80

Asn Ser Lys Asn Ala Gly Ser Lys His Asn Phe Leu Asn His Gly Leu
                 85                  90                  95

Pro Leu Asn Leu Ala Ile Lys Pro Tyr Leu Ala Leu Lys Gly Ser Val
             100                 105                 110

Ala Phe Pro Ala Glu Asn Glu Val Gln Asn Thr Glu Ser Thr Gln Glu
         115                 120                 125

Lys Arg Glu Ile Gly Asp Glu Glu Asn Ser Ala Lys Phe Pro Ile Gly
 130                 135                 140
```

Arg Arg Asp Phe Asp Met Leu Arg Cys Met Leu Gly Arg Val Tyr Arg
145                 150                 155                 160

Pro Cys Trp Gln Val
                165

<210> SEQ ID NO 6
<211> LENGTH: 534
<212> TYPE: DNA
<213> ORGANISM: Bos taurus

<400> SEQUENCE: 6
tccttgtttg actctatgca acatcaaac taaggatggc aaaaatgagt ttctcttcct      60
acatattaat actaactttt tctttgcttt ctcaaggcat ttcactttca gcatccaagt    120
cgataagaaa tttagatgat gacatggtat ttaaaacgtt gaggctgggg aaagcctttc    180
agaaggaaga taccgcagaa aaatcaattg ttgttccttc cctggagcaa tataaaaatg    240
atgagagcag tttcatgaat gatgaagaaa acaaaaattc aaagaatgca ggttccaaac    300
ataatttctt aaatcatggc ctgccactga atctggctat aaaaccttat cttgcactaa    360
aaggatctgt agcttttcca gctgagaatg aagttcaaaa tactgaatca acacaagaaa    420
aaagagaaat tggggatgaa gaaaactcag ctaaatttcc tataggaagg agagattttg    480
acatgcttag gtgtatgctg ggaagagtct atcgaccttg ttggcaagtc tgat          534

<210> SEQ ID NO 7
<211> LENGTH: 16
<212> TYPE: PRT
<213> ORGANISM: Bos taurus

<400> SEQUENCE: 7

Gly Ser Val Ala Phe Pro Ala Glu Asn Glu Val Gln Asn Thr Glu Ser
1               5                   10                  15

<210> SEQ ID NO 8
<211> LENGTH: 14
<212> TYPE: PRT
<213> ORGANISM: Bos taurus

<400> SEQUENCE: 8

Glu Ile Gly Asp Glu Glu Asn Ser Ala Lys Phe Pro Ile Gly
1               5                   10

<210> SEQ ID NO 9
<211> LENGTH: 19
<212> TYPE: PRT
<213> ORGANISM: Bos taurus

<400> SEQUENCE: 9

Asp Phe Asp Met Leu Arg Cys Met Leu Gly Arg Val Tyr Arg Pro Cys
1               5                   10                  15

Trp Gln Val

<210> SEQ ID NO 10
<211> LENGTH: 22
<212> TYPE: DNA
<213> ORGANISM: Artificial Sequence
<220> FEATURE:
<223> OTHER INFORMATION: primer

<400> SEQUENCE: 10
gcaaacatca aactaaggat gg                                              22

```
<210> SEQ ID NO 11
<211> LENGTH: 21
<212> TYPE: DNA
<213> ORGANISM: Artificial Sequence
<220> FEATURE:
<223> OTHER INFORMATION: primer

<400> SEQUENCE: 11
cgtatggtta gcatgttaag c                                             21

<210> SEQ ID NO 12
<211> LENGTH: 21
<212> TYPE: DNA
<213> ORGANISM: Artificial Sequence
<220> FEATURE:
<223> OTHER INFORMATION: primer

<400> SEQUENCE: 12
ggttggtttc tatctgatga g                                             21

<210> SEQ ID NO 13
<211> LENGTH: 22
<212> TYPE: DNA
<213> ORGANISM: Artificial Sequence
<220> FEATURE:
<223> OTHER INFORMATION: primer

<400> SEQUENCE: 13
gtcgcattat cacttacctt tg                                            22

<210> SEQ ID NO 14
<211> LENGTH: 18
<212> TYPE: DNA
<213> ORGANISM: Artificial Sequence
<220> FEATURE:
<223> OTHER INFORMATION: mismatch primer

<400> SEQUENCE: 14
ccttgtttga ctctatgc                                                 18

<210> SEQ ID NO 15
<211> LENGTH: 25
<212> TYPE: DNA
<213> ORGANISM: Artificial Sequence
<220> FEATURE:
<223> OTHER INFORMATION: primer

<400> SEQUENCE: 15 gcatacaccct aagcatgtca aaatc                                        25

<210> SEQ ID NO 16
<211> LENGTH: 25
<212> TYPE: DNA
<213> ORGANISM: Artificial Sequence
<220> FEATURE:
<223> OTHER INFORMATION: primer

<400> SEQUENCE: 16
caaaaattca aagaatgcag gttcc                                         25

<210> SEQ ID NO 17
<211> LENGTH: 18
<212> TYPE: DNA
<213> ORGANISM: Artificial Sequence
<220> FEATURE:
<223> OTHER INFORMATION: primer

<400> SEQUENCE: 17
```

```
gacttgccaa caaggtcg                                                    18

<210> SEQ ID NO 18
<211> LENGTH: 23
<212> TYPE: DNA
<213> ORGANISM: Artificial Sequence
<220> FEATURE:
<223> OTHER INFORMATION: primer

<400> SEQUENCE: 18
gatgagtcat ttctaaaatg acg                                              23

<210> SEQ ID NO 19
<211> LENGTH: 19
<212> TYPE: DNA
<213> ORGANISM: Artificial Sequence
<220> FEATURE:
<223> OTHER INFORMATION: primer

<400> SEQUENCE: 19
gtttgtgatg ggcgtgaac                                                   19

<210> SEQ ID NO 20
<211> LENGTH: 19
<212> TYPE: DNA
<213> ORGANISM: Artificial Sequence
<220> FEATURE:
<223> OTHER INFORMATION: primer

<400> SEQUENCE: 20
gtggacagtg gtcataagt                                                   19

<210> SEQ ID NO 21
<211> LENGTH: 104
<212> TYPE: DNA
<213> ORGANISM: Bos taurus

<400> SEQUENCE: 21
gttggtttct atctgatgag tcatttctaa aatgatgwaa gttttccaag tgctttctat      60
tcaagctgga aaatatataa aggcaagaat catttacaaa gcag                      104

<210> SEQ ID NO 22
<211> LENGTH: 119
<212> TYPE: DNA
<213> ORGANISM: Human

<400> SEQUENCE: 22
cataaaggtt agcctcaatc taatgagtca tttctaaaat gatgaaaagt ataattcttt      60
gaagtgcttt ctattcaagc taggaaatat ataaagatac agaatcgttt accaagcag     119

<210> SEQ ID NO 23
<211> LENGTH: 113
<212> TYPE: DNA
<213> ORGANISM: Rat

<400> SEQUENCE: 23
tacaaaggcg aggctctacg gggtgattca tttctaaaaa gaaaagataa ggccttcaag      60
tgttttctat tcaggcacaa agtatatataaa ggtaggaatc attcagtcgc cag          113
```